(12) United States Patent
Dyatkina et al.

(10) Patent No.: US 7,629,320 B2
(45) Date of Patent: Dec. 8, 2009

(54) NUCLEOSIDE DERIVATIVES FOR TREATING HEPATITIS C VIRUS INFECTION

(75) Inventors: Natalia B. Dyatkina, Mountain View, CA (US); Christopher D. Roberts, Belmont, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 12/123,310

(22) Filed: May 19, 2008

(65) Prior Publication Data

US 2008/0249060 A1    Oct. 9, 2008

Related U.S. Application Data

(62) Division of application No. 10/676,956, filed on Sep. 30, 2003, now Pat. No. 7,425,547.

(60) Provisional application No. 60/443,169, filed on Jan. 29, 2003, provisional application No. 60/415,222, filed on Sep. 30, 2002.

(51) Int. Cl.
*A61K 31/70*    (2006.01)
*C07H 19/04*    (2006.01)

(52) U.S. Cl. .................. 514/43; 536/26.23; 536/26.26; 536/26.7; 536/27.2

(58) Field of Classification Search .............. None
See application file for complete search history.

(56) References Cited

U.S. PATENT DOCUMENTS

| | | | |
|---|---|---|---|
| 5,430,027 A * | 7/1995 | Knutsen et al. ............... 514/46 |
| 5,681,941 A | 10/1997 | Cook et al. |
| 5,763,167 A * | 6/1998 | Conrad ........................... 435/6 |
| 5,977,332 A * | 11/1999 | Martin ....................... 536/23.1 |
| 6,211,154 B1 * | 4/2001 | Scarborough et al. ......... 514/18 |
| 6,475,985 B1 * | 11/2002 | Wagner et al. ................... 514/7 |
| 6,500,946 B1 | 12/2002 | Takamatsu et al. |
| 6,586,413 B2 * | 7/2003 | Liang et al. ................... 514/46 |
| 6,660,721 B2 | 12/2003 | Devos et al. |
| 6,703,394 B2 | 3/2004 | Engelhardt et al. |
| 7,425,547 B2 * | 9/2008 | Roberts et al. ................. 514/46 |
| 2003/0130226 A1 * | 7/2003 | Loakes et al. ................. 514/46 |
| 2007/0015905 A1 | 1/2007 | LaColla et al. |
| 2007/0032449 A1 | 2/2007 | LaColla et al. |

FOREIGN PATENT DOCUMENTS

| EP | 1117669 | 7/2001 |
|---|---|---|
| WO | WO 94/18215 | 8/1994 |
| WO | WO 95/07919 | 3/1995 |
| WO | WO 2002/057425 A2 | 7/2002 |
| WO | WO2003/061576 A3 * | 7/2003 |
| WO | WO 2004/002848 | 1/2004 |
| WO | WO 2004/065398 | 8/2004 |

OTHER PUBLICATIONS

[R] Bowler et al., "New Adenosine A3 Ligands Controlling Cytokines," Drug Development Research, 37, 173 (bottom of col. 2) (Mar. 1996); disclosed in the parent case.*
(S) Jacobson et al., "Recent Developments in Selective Agonists and Antagonists Acting at Purine and Pyrimidine Receptors," Drug Development Research, 39(3-4), 289-300 (1996); disclosed in the parent case.*
Beigelman et al. "New Syntheses of 2'-C-Methylnucleosides Starting from D-Glucose and D-Ribose" *Carbo. Research*, 166:219-232 (1987).
Bowler et al., "New Adenosine A3 Ligands Controlling Cytokines," *Drug Development Research*, 37, 173 (bottom of col. 2) (Mar. 1996).
Jacobson et al., "Recent Developments in Selective Agonists and Antagonists Acting at Purine and Pyrimidine Receptors," *Drug Development Research*, 39(3-4), 289-300 (1996).

* cited by examiner

*Primary Examiner*—Lawrence E Crane
(74) *Attorney, Agent, or Firm*—Robert (Steve) Thomas

(57) ABSTRACT

Disclosed are β-D-ribofuranosyl-pyrazolo[3,4-d]pyrimidine compounds, compositions and methods for treating viral infections caused by a flaviviridae family virus, such as hepatitis C virus. Representative compounds include those having the general formula.

19 Claims, No Drawings

NUCLEOSIDE DERIVATIVES FOR TREATING HEPATITIS C VIRUS INFECTION

CROSS-REFERENCE TO RELATED APPLICATIONS

This application is a divisional application of, and claims the benefit under 35 U.S.C. 120 and 121 of U.S. application Ser. No. 10/676,956 filed Sep. 30, 2003, which claims the benefit under 35 U.S.C. 119(e) of U.S. Provisional Application Ser. No. 60/443,169, filed Jan. 29, 2003 and U.S. Provisional Application Ser. No. 60/415,222, filed Sep. 30, 2002. Each of these prior applications are incorporated into this application by reference in their entirety.

FIELD OF THE INVENTION

The invention relates to the field of pharmaceutical chemistry, in particular to compounds, compositions and methods for treating hepatitis C viral infections.

REFERENCES

The following publications are cited in this application as superscript numbers:
1. Chen, et al., Med. Assoc., 95(1):6-12 (1996)
2. Cornberg, et al., "Hepatitis C: therapeutic perspectives." Forum (Genova), 11(2):154-62 (2001)
3. Dymock, et al., Antivir. Chem. Chemother. 11(2):79-96 (2000)
4. Devos, et al., International Patent Application Publication No. WO 02/18404 A2, published 7 Mar. 2002
5. Sommadossi, et al., International Patent Application Publication No. WO 01/90121, published 23 May 2001
6. Carroll, et al., International Patent Application Publication No. WO 02/057425
7. Seela, F.; Steker, H., *Liebigs Ann. Chem.*, p. 1576 (1983).
8. Li, N-. S.; Tang, X.-Q.; Piccirilli, J. A., *Organic Letters*, 3(7):1025 (2001).

All of the above publications are herein incorporated by reference in their entirety to the same extent as if each individual publication was specifically and individually indicated to be incorporated by reference in its entirety.

STATE OF THE ART

Hepatitis C virus (HCV) causes a liver damaging infection that can lead to cirrhosis, liver failure or liver cancer, and eventually death. HCV is an enveloped virus containing a positive-sense single-stranded RNA genome of approximately 9.4 kb, and has a virion size of 30-60 nm.[1]

HCV is a major causative agent for post-transfusion and for sporadic non-A, non-B hepatitis. Infection by HCV is insidious in a high proportion of chronically infected (and infectious) carriers who may not experience clinical symptoms for many years.

HCV is difficult to treat and it is estimated that there are 500 million people infected with it worldwide. No effective immunization is currently available, and hepatitis C can only be controlled by other preventive measures such as improvement in hygiene and sanitary conditions and interrupting the route of transmission.

At present, the only acceptable treatment for chronic hepatitis C is interferon (IFN-alpha) and this requires at least six (6) months of treatment and/or ribavarin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular, viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1H-1,2,-4-triazole-3-carboxamide), an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of PEG-IFN plus ribavirin. However, a number of patients still have significant side effects, primarily related to ribavirin. Ribavirin causes significant hemolysis in 10-20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. NS3/4A serine protease, ribonucleic acid (RNA) helicase, RNA-dependent RNA polymerase are considered as potential targets for new drugs.[2,3]

Devos, et al.[4] describes purine and pyrimidine nucleoside derivatives and their use as inhibitors of HCV RNA replication. Sommadossi, et al.[5] describes 1', 2' or 3'-modified nucleosides and their use for treating a host infected with HCV.

Given the fact of the worldwide epidemic level of HCV, there is a strong need for new effective drugs for HCV treatment. The present invention provides nucleoside derivatives for treating HCV infections.

SUMMARY OF THE INVENTION

This invention is directed to novel compounds that are useful in the treatment of HCV in mammals. Specifically, in one aspect, the compounds of this invention are represented by Formula I below:

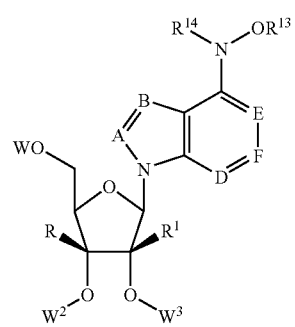

I wherein R and $R^1$ are independently selected from the group consisting of:

hydrogen,
alkyl,
substituted alkyl,
alkenyl,
substituted alkenyl,
alkynyl,
substituted alkynyl;

$R^{13}$ is selected from the group consisting of hydrogen, alkyl, and substituted alkyl;

$R^{14}$ is selected from the group consisting of hydrogen, alkyl, and substituted alkyl;

A, B, D, and E are independently selected from the group consisting of >N, >CH, >C—CN, >C—NO$_2$, >C-alkyl, >C-substituted alkyl, >C-alkenyl, >C-substituted alkenyl, >C-alkynyl, >C-substituted alkynyl, >C—NHCONH$_2$, >C—CONR$^{15}$R$^{16}$, >C—COOR$^{15}$, >C-hydroxy, >C-alkoxy, >C-amino, >C-alkylamino, >C-dialkylamino, >C-halogen, >C-(1,3-oxazol-2-yl), >C-(1,3-oxazol-5-yl), >C-(1,3-thiazol-2-yl), >C-(imidazol-2-yl), >C-(2-oxo-[1,3]dithiol-4-yl), >C-(furan-2-yl), and >C-(2H-[1,2,3]triazol-4-yl);

F is selected from >N, >C—CN, >C—NO$_2$, >C-alkyl, >C-substituted alkyl, >C-alkenyl, >C-substituted alkenyl, >C-alkynyl, >C-substituted alkynyl, >C—NHCONH$_2$, >C—CONR$^{15}$R$^{16}$, >C—COOR$^{15}$, >C-alkoxy, >C-(1,3-oxazol-2-yl), >C-(1,3-oxazol-5-yl), >C-(1,3-thiazol-2-yl), >C-(imidazol-2-yl), >C-(2-oxo-[1,3]dithiol-4-yl), >C-(furan-2-yl), >C-(2H-[1,2,3]triazol-4-yl), and >C—Y, where Y is selected from the group consisting of hydrogen, halo, hydroxy, alkylthioether, and —NR$^3$R$^4$ where R$^3$ and R$^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where R$^3$ and R$^4$ are joined to form, together with the nitrogen atom bond thereto, a heterocyclic group, provided that only one of R$^3$ and R$^4$ is hydroxy, alkoxy, or substituted alkoxy;

$R^{15}$ and $R^{16}$ are independently selected from the group consisting of:
hydrogen,
alkyl,
substituted alkyl,
cycloalkyl,
substituted cycloalkyl,
aryl,
substituted aryl,
heteroaryl,
substituted heteroaryl, and
$R^{15}$ and $R^{16}$ together with the nitrogen atom to which they are attached may form a heterocycloalkyl, substituted heterocycloalkyl, heteroaryl, or substituted heteroaryl group;

W, W$^2$, and W$^3$ are independently selected from the group consisting of:
hydrogen,
a phosphate,
a phosphonate,
a monofluorophosphate,
acyl,
a sulfonate ester,
a lipid,
an amino acid,
a carbohydrate,
a peptide, and
cholesterol;

and pharmaceutically acceptable prodrugs and salts thereof, provided that the compound of Formula I is not:
a) 9-(β-D-ribofuranosyl)-6-hydroxylaminopurine;
b) 7-(β-D-ribofuranosyl)-4-hydroxylamino-pyrrolo[2,3-d]pyrimidine;
c) 9-(2'-C-methyl-α-D-ribofuranosyl)-6-hydroxylaminopurine;
d) 9-(5'-O-monophosphate-β-D-ribofuranosyl)-6-hydroxylaminopurine; and
e) 9-(5'-O-triphosphate-β-D-ribofuranosyl)-6-hydroxylaminopurine.

Preferably, R and R$^1$ are not both hydrogen.

In another of its compound aspects, this invention is directed to a compound of Formula IA:

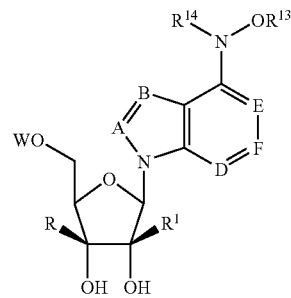

IA wherein R and R$^1$ are independently selected from the group consisting of:
hydrogen,
alkyl,
substituted alkyl,
alkenyl,
substituted alkenyl,
alkynyl,
substituted alkynyl;
provided that R and R$^1$ are not both hydrogen;

$R^{13}$ is selected from the group consisting of hydrogen, alkyl, and substituted alkyl;

$R^{14}$ is selected from the group consisting of hydrogen, alkyl, and substituted alkyl;

A, B, D, and E are independently selected from the group consisting of >N, >CH, >C—CN, >C—NO$_2$, >C-alkyl, >C-substituted alkyl, >C—NHCONH$_2$, >C—CONR$^{15}$R$^{16}$, >C—COOR$^{15}$, >C-hydroxy, >C-alkoxy, >C-amino, >C-alkylamino, >C-dialkylamino, >C-halogen, >C-(1,3-oxazol-2-yl), >C-(1,3-thiazol-2-yl) and >C-(imidazol-2-yl);

F is selected from >N, >C—CN, >C—NO$_2$, >C-alkyl, >C-substituted alkyl, >C—NHCONH$_2$, >C—CONR$^{15}$R$^{16}$, >C—COOR$^{15}$, >C-alkoxy, >C-(1,3-oxazol-2-yl), >C-(1,3-thiazol-2-yl), >C-(imidazol-2-yl), and >C—Y, where Y is selected from the group consisting of hydrogen, halo, hydroxy, alkylthioether, and —NR$^3$R$^4$ where R$^3$ and R$^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where R$^3$ and R$^4$ are joined to form, together with the nitrogen atom bond thereto, a heterocyclic group, provided that only one of R$^3$ and R$^4$ are hydroxy, alkoxy, or substituted alkoxy;

$R^{15}$ and $R^{16}$ are independently selected from the group consisting of:

hydrogen,
alkyl,
substituted alkyl,
cycloalkyl,
substituted cycloalkyl,
aryl,
substituted aryl,
heteroaryl,
substituted heteroaryl, and
$R^{15}$ and $R^{16}$ together with the nitrogen atom to which they are attached may form a heterocycloalkyl, substituted heterocycloalkyl, heteroaryl, or substituted heteroaryl group;
W is selected from the group consisting of:
hydrogen,
a phosphate,
a phosphonate,
acyl,
alkyl,
a sulfonate ester,
a lipid,
an amino acid,
a carbohydrate,
a peptide, and
cholesterol;
and pharmaceutically acceptable salts thereof,
provided that the compound of Formula IA is not 9-(2'-C-methyl-α-D-ribofuranosyl)-6-hydroxylaminopurine.

In still another of its compound aspects, this invention is directed to a compound of Formula IB:

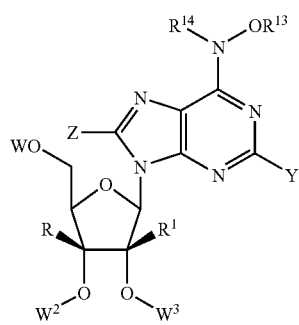

IB wherein R and $R^1$ are independently selected from the group consisting of:
hydrogen,
alkyl,
substituted alkyl,
alkenyl,
substituted alkenyl,
alkynyl, and
substituted alkynyl;
$R^{13}$ is selected from the group consisting of hydrogen, alkyl, and substituted alkyl;
$R^{14}$ is selected from the group consisting of hydrogen, alkyl, and substituted alkyl;
Y is selected from the group consisting of:
hydrogen,
halo,
hydroxy,
alkylthioether,
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;
Z is selected from the group consisting of:
hydrogen,
halo,
hydroxy,
alkyl,
substituted alkyl,
alkenyl,
substituted alkenyl,
alkynyl,
substituted alkynyl,
cyano,
carboxyl,
carboxyl ester,
acylamino,
1,3-oxazol-2-yl,
1,3-oxazol-5-yl,
1,3-thiazol-2-yl,
imidazol-2-yl,
2-oxo-[1,3]dithiol-4-yl,
furan-2-yl,
2H-[1,2,3]triazol-4-yl, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ are hydroxy, alkoxy, or substituted alkoxy;
W, $W^2$, and $W^3$ are independently selected from the group consisting of:
hydrogen,
a phosphate,
a phosphonate,
a monofluorophosphate
acyl,
a sulfonate ester,
a lipid,
an amino acid,
a carbohydrate,
a peptide, and
cholesterol;
and pharmaceutically acceptable prodrugs and salts thereof,
provided that the compound of Formula IB is not:
a) 9-(β-D-ribofuranosyl)-6-hydroxylaminopurine;
b) 9-(2'-C-methyl-α-D-ribofuranosyl)-6-hydroxylaminopurine;
c) 9-(5'-O-monophosphate-β-D-ribofuranosyl)-6-hydroxylaminopurine; and
d) 9-(5'-O-triphosphate-β-D-ribofuranosyl)-6-hydroxylaminopurine.

Preferably at least one of R and $R^1$ is other than hydrogen.
In another of its compound aspects, this invention is directed to a compound of Formula IC:

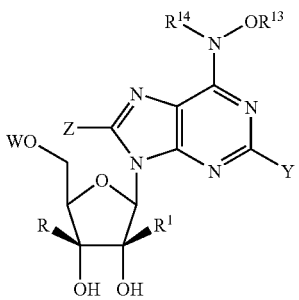

wherein R and $R^1$ are independently selected from the group consisting of:
hydrogen,
alkyl,
substituted alkyl,
alkenyl,
substituted alkenyl,
alkynyl, and
substituted alkynyl,
provided that R and $R^1$ are not both hydrogen;
$R^{13}$ is selected from the group consisting of hydrogen, alkyl, and substituted alkyl;
$R^{14}$ is selected from the group consisting of hydrogen, alkyl, and substituted alkyl;
Y is selected from the group consisting of:
hydrogen,
halo,
hydroxy,
alkylthioether,
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;
Z is selected from the group consisting of:
hydrogen,
halo,
hydroxy,
alkyl, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;
W is selected from the group consisting of:
hydrogen,
a phosphate,
a phosphonate,
acyl,
a sulfonate ester,
a lipid,
an amino acid,
a carbohydrate,
a peptide, and
cholesterol;
and pharmaceutically acceptable salts thereof,
provided that the compound of Formula IC is not 9-(2'-C-methyl-α-D-ribofuranosyl)-6-(—S or R Inactive-)-hydroxylaminopurine.

In another of its compound aspects, this invention is directed to a compound of Formula IC-A:

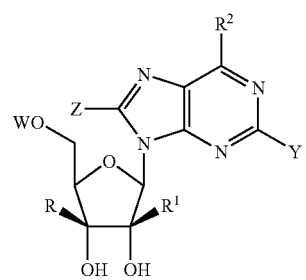

wherein R and $R^1$ are independently selected from the group consisting of:
hydrogen,
alkyl,
substituted alkyl,
alkenyl,
substituted alkenyl,
alkynyl, and
substituted alkynyl,
provided that R and $R^1$ are not both hydrogen;
$R^2$ is —$NR^3R^4$ where $R^3$ is hydrogen and $R^4$ is hydroxy or alkoxy;
Y is selected from the group consisting of:
hydrogen,
halo,
hydroxy,
alkylthioether,
—$NR^3R^4$ where $R^3$ and $R^4$ are independently selected from the group consisting of hydrogen, alkyl, substituted alkyl, alkenyl, substituted alkenyl, alkynyl, substituted alkynyl, alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group;
Z is selected from the group consisting of:
hydrogen,
halo,
hydroxy, and
—$NR^3R^4$ where $R^3$ and $R^4$ are independently selected from the group consisting of hydrogen, alkyl, substituted alkyl, alkenyl, substituted alkenyl, alkynyl, substituted alkynyl, alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group;
W is selected from the group consisting of:
hydrogen,
a phosphate,
acyl,
a sulfonate ester, a lipid,
an amino acid,
a carbohydrate,
a peptide, and
cholesterol;
and pharmaceutically acceptable salts thereof,
provided that the compound If Formula IC-A is not 9-(2'-C-methyl-α-D-ribofuranosyl)-6-hydroxylaminopurine.

In another of its composition aspects, this invention is directed to a compound of Formula ID:

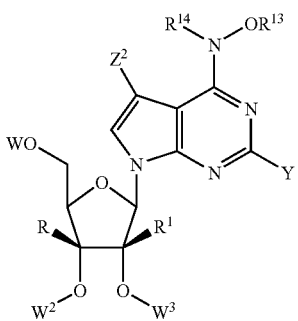

ID wherein R and $R^1$ are independently selected from the group consisting of:
hydrogen,
alkyl,
substituted alkyl,
alkenyl,
substituted alkenyl,
alkynyl, and
substituted alkynyl;
$R^{13}$ is selected from the group consisting of hydrogen, alkyl, and substituted alkyl;
$R^{14}$ is selected from the group consisting of hydrogen, alkyl, and substituted alkyl;
Y is selected from the group consisting of:
hydrogen,
halo,
hydroxy,
alkylthioether, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;
$Z^2$ is selected from the group consisting of:
hydrogen,
halo,
hydroxy,
alkyl,
substituted alkyl,
alkenyl,
substituted alkenyl,
alkynyl,
substituted alkynyl,
cyano
carboxyl,
carboxyl ester,
acylamino,
1,3-oxazol-2-yl,
1,3-oxazol-5-yl,
1,3-thiazol-2-yl,
imidazol-2-yl,
2-oxo-[1,3]dithiol-4-yl,
furan-2-yl,
2H-[1,2,3]triazol-4-yl, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;
W, $W^2$, and $W^3$ are independently selected from the group consisting of:
hydrogen,
a phosphate,
phosphonate,
monofluorophosphate
acyl,
alkyl,
a sulfonate ester,
a lipid,
an amino acid,
a carbohydrate,
a peptide, and
cholesterol;
and pharmaceutically acceptable prodrugs and salts thereof,
provided that the compound If Formula ID is not 7-(β-D-ribofuranosyl)-4-hydroxylamino-pyrrolo[2,3-d]pyrimidine.

Preferably, at least one of R or $R^1$ is other than hydrogen.

In yet another of its compound aspects, this invention is directed to a compound of Formula IE:

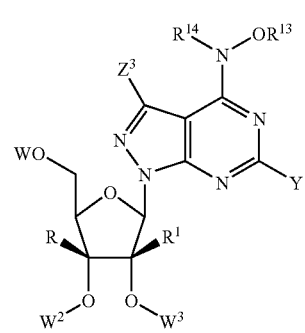

IE wherein R and $R^1$ are independently selected from the group consisting of:
hydrogen,
alkyl,
substituted alkyl,
alkenyl,
substituted alkenyl,
alkynyl, and
substituted alkynyl;
$R^{13}$ is selected from the group consisting of hydrogen, alkyl, and substituted alkyl;

$R^{14}$ is selected from the group consisting of hydrogen, alkyl, and substituted alkyl;

Y is selected from the group consisting of:
hydrogen,
halo,
hydroxy,
alkylthioether, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;

$Z^3$ is selected from the group consisting of:
hydrogen,
halo,
hydroxy,
alkyl,
substituted alkyl,
alkenyl,
substituted alkenyl,
alkynyl,
substituted alkynyl,
cyano
carboxyl,
carboxyl ester,
acylamino,
1,3-oxazol-2-yl,
1,3-oxazol-5-yl,
1,3-thiazol-2-yl,
imidazol-2-yl,
2-oxo-[1,3]dithiol-4-yl,
furan-2-yl,
2H-[1,2,3]triazol-4-yl, and
—$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;

W, $W^2$, and $W^3$ are independently selected from the group consisting of:
hydrogen,
a phosphate,
a phosphonate,
a monofluorophosphate,
acyl,
a sulfonate ester,
a lipid,
an amino acid,
a carbohydrate,
a peptide, and
cholesterol;
and pharmaceutically acceptable prodrugs and salts thereof.

Preferably, at least one of R and $R^1$ is other than hydrogen.

In another of its composition aspects, this invention is directed to a compound of formula II:

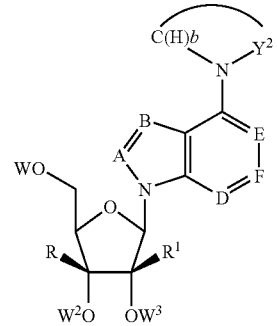

wherein R and $R^1$ are independently selected from the group consisting of:
hydrogen,
alkyl,
substituted alkyl,
alkenyl,
substituted alkenyl,
alkynyl, and
substituted alkynyl;

$Y^2$ is $CH_2$, N, O, S, SO, or $SO_2$;

N together with —$C(H)_b$ and $Y^2$ forms a heterocyclic, substituted heterocyclic, heteroaryl or substituted heteroaryl group wherein each of said heterocyclic, substituted heterocyclic, heteroaryl or substituted heteroaryl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures is optionally substituted with 1 to 4 substituents selected from the group consisting of hydroxyl, halo, alkoxy, substituted alkoxy, thioalkyl, substituted thioalkyl, aryl, heteroaryl, heterocyclic, nitro, cyano, carboxyl, carboxyl esters, alkyl, substituted alkyl, alkenyl, substituted alkenyl, alkynyl, substituted alkynyl, amino, and substituted amino;

b is an integer equal to 0 or 1;

A, B, D, and E are independently selected from the group consisting of >N, >CH, >C—CN, >C—$NO_2$, >C-alkyl, >C-substituted alkyl, >C-alkenyl, >C-substituted alkenyl, >C-alkynyl, >C-substituted alkynyl, >C—$NHCONH_2$, >C—$CONR^{15}R^{16}$, >C—$COOR^{15}$, >C-hydroxy, >C-alkoxy, >C-amino, >C-alkylamino, >C-dialkylamino, >C-halogen, >C-(1,3-oxazol-2-yl), >C-(1,3-oxazol-5-yl), >C-(1,3-thiazol-2-yl), >C-(imidazol-2-yl), >C-(2-oxo-[1,3]dithiol-4-yl), >C-(furan-2-yl), and >C-(2H-[1,2,3]triazol-4-yl);

F is selected from >N, >C—CN, >C—$NO_2$, >C-alkyl, >C-substituted alkyl, >C-alkenyl, >C-substituted alkenyl, >C-alkynyl, >C-substituted alkynyl, >C—$NHCONH_2$, >C—$CONR^{15}R^{16}$, >C—$COOR^{15}$, >C-alkoxy, >C-(1,3-oxazol-2-yl), >C-(1,3-oxazol-5-yl), >C-(1,3-thiazol-2-yl), >C-(imidazol-2-yl), >C-(2-oxo-[1,3]dithiol-4-yl), >C-(furan-2-yl), >C-(2H-[1,2,3]triazol-4-yl), and >C—Y, where Y is selected from the group consisting of hydrogen, halo, hydroxy, alkylthioether, and —$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ are hydroxy, alkoxy, or substituted alkoxy;

$R^{15}$ and $R^{16}$ are independently selected from the group consisting of:
hydrogen,
alkyl,
substituted alkyl,
cycloalkyl,
substituted cycloalkyl,
aryl,
substituted aryl,
heteroaryl,
substituted heteroaryl, and
$R^{15}$ and $R^{16}$ together with the nitrogen atom to which they are attached may form a heterocycloalkyl, substituted heterocycloalkyl, heteroaryl, or substituted heteroaryl;

W, $W^2$, and $W^3$ are independently selected from the group consisting of:
hydrogen,
a phosphate,
a phosphonate,
a monofluorophosphate,
acyl,
a sulfonate ester,
a lipid,
an amino acid,
a carbohydrate,
a peptide, and
cholesterol;
and pharmaceutically acceptable salts thereof.

Preferably, at least one of R and $R^1$ is other than hydrogen.

In still a further compound aspect, this invention is directed to compounds of Formula IIA:

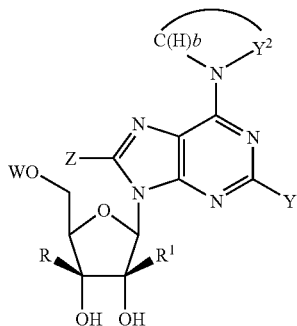

IIA wherein R and $R^1$ are independently selected from the group consisting of:
hydrogen,
alkyl,
substituted alkyl,
alkenyl,
substituted alkenyl,
alkynyl, and
substituted alkynyl,
provided that R and $R^1$ are not both hydrogen;
$Y^2$ is $CH_2$, N, O, S, SO, or $SO_2$;

N together with —C(H)$_b$ and $Y^2$ forms a heterocyclic, substituted heterocyclic, heteroaryl or substituted heteroaryl group wherein each of said heterocyclic, substituted heterocyclic, heteroaryl or substituted heteroaryl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures is optionally substituted with 1 to 4 substituents selected from the group consisting of hydroxyl, halo, alkoxy, substituted alkoxy, thioalkyl, substituted thioalkyl, aryl, heteroaryl, heterocyclic, nitro, cyano, carboxyl, carboxyl esters, alkyl, substituted alkyl, alkenyl, substituted alkenyl, alkynyl, substituted alkynyl, amino, and substituted amino;

b is an integer equal to 0 or 1;
W is selected from the group consisting of:
hydrogen,
a phosphate,
a phosphonate,
acyl,
alkyl,
a sulfonate ester,
a lipid,
an amino acid,
a carbohydrate,
a peptide, and
cholesterol;

Y is selected from the group consisting of Y is selected from the group consisting of:
hydrogen,
halo,
hydroxy,
alkylthioether, and
—$NR^3R^4$ where $R^3$ and $R^4$ are independently selected from the group consisting of hydrogen, hydroxy, alkyl, substituted alkyl, alkenyl, substituted alkenyl, alkynyl and substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;

Z is selected from the group consisting of:
hydrogen,
halo,
hydroxy,
alkyl, and
—$NR^3R^4$ where $R^3$ and $R^4$ are independently selected from the group consisting of hydrogen, hydroxy, alkyl, substituted alkyl, alkenyl, substituted alkenyl, alkynyl and substituted alkynyl, alkoxy, substituted alkoxy, aryl, substituted aryl, heteroaryl, substituted heteroaryl, heterocyclic, substituted heterocyclic and where $R^3$ and $R^4$ is joined to form, together with the nitrogen atom bond thereto, a heterocyclic group, provided that only one of $R^3$ and $R^4$ are hydroxy, alkoxy, or substituted alkoxy;
and pharmaceutically acceptable salts thereof.

In one preferred embodiment, $R^{14}$ in Formula I-IE is hydrogen and $R^{13}$ is selected from the group consisting of alkyl and hydrogen.

In another preferred embodiment, $R^{14}$ in Formula I-IE is hydrogen and $R^{13}$ is selected from the group consisting of hydrogen, methyl, ethyl, n-propyl, and the like.

Preferably, in the compounds of this invention, R is hydrogen and $R^1$ is selected from the group consisting of methyl, vinyl, allyl, acetylenyl, propargyl, trifluoromethyl and the like.

In one preferred embodiment, A is >CH, B is >N, D is >N, F is >CH or >C—Y and E is >N in the compounds of Formula I.

In another preferred embodiment, A is >CH, B is >C-Q, D is >N, F is >CH or >C—Y and E is >N in the compounds of Formula I where Q is selected from the group consisting of hydrogen, halo, cyano, acylamido, alkyl, alkenyl, alkynyl, and heteroaryl. More preferably, Q is hydrogen, chloro, bromo, cyano, $H_2NC(O)$—, methyl, ethyl, vinyl, acetylenyl and oxazidin-2-yl.

In another preferred embodiment, A is >N, B is >C-Q, D is >N, F is >CH or >C—Y and E is >N in the compounds of Formula I where Q is selected from the group consisting of hydrogen, halo, cyano, acylamido, alkyl, alkenyl and alkynyl. More preferably, Q is hydrogen, chloro, bromo, cyano, $H_2NC(O)$—, methyl, ethyl, vinyl and acetylenyl.

In a preferred embodiment, W is hydrogen, acyl or triphosphate in the compounds of this invention.

In the compounds of Formula I, IB, ID, IE and II, $W^2$ and $W^3$ are preferably hydrogen or acyl. More preferably, $W^2$ is hydrogen or acyl and $W^3$ is hydrogen. Particularly preferred acyl groups are derived from amino acid group such as $(CH_3)_2CH(NH_2)C(O)$—, trimethylacetyl, acetyl, and the like.

In one preferred embodiment of the compounds of Formula II and IIA, N together with —$C(H)_b$ and $Y^2$ forms a heterocyclic or substituted heterocyclic group. Such preferred groups are exemplified by 2-carboxamido-pyrrolidin-1-yl, piperidin-1-yl, N-morpholino, N-thiomorpholino, azetidin-1-yl, pyrrolin-1-yl, 1,2,3,4-tetrahydropyridin-1-yl, 1,2,3,4-tetrahydroisoquinolin-2-yl, 1,3,4,9-tetrahydro-beta-carbolin-2-yl, and the like.

Compounds included within the scope of this invention include, for example, those set forth below (including pharmaceutically acceptable salts thereof):

| # | Structure | Name |
|---|---|---|
| 1 (109) | 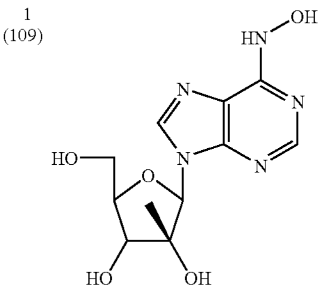 | 9-(2'-C-methyl-β-D-ribofuranosyl)-6-hydroxylaminopurine |
| 2 (111) | 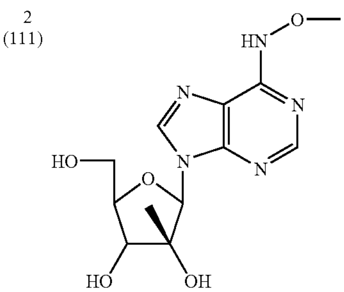 | 9-(2'-C-methyl-β-D-ribofuranosyl)-6-methoxylaminopurine |
| 3 (116) | 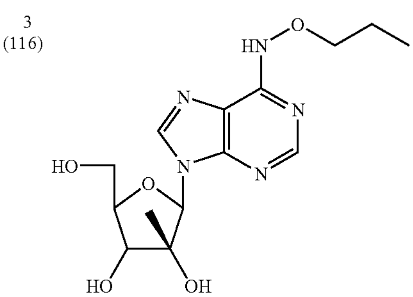 | 9-(2'-C-methyl-β-D-ribofuranosyl)-6-propoxylaminopurine |
| 4 (117) | 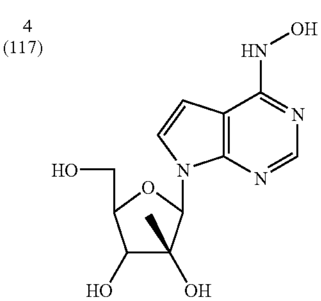 | 7-(2'-C-methyl-β-D-ribofuranosyl)-4-hydroxylamino-pyrrolo[2,3-d]pyrimidine |

-continued

| # | Structure | Name |
|---|---|---|
| 5 (118) | 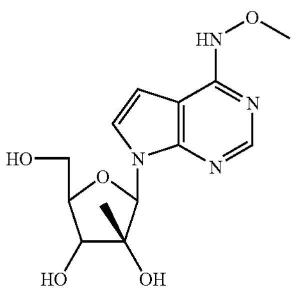 | 7-(2'-C-methyl-β-D-ribofuranosyl)-4-methoxylamino-pyrrolo[2,3-d]pyrimidine |
| 6 (119) | 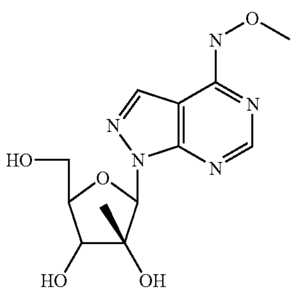 | 1-(2'-C-methyl-β-D-ribofuranosyl)-4-methoxylamino-pyrazolo[3,4-d]pyrimidine |
| 7 (120) | 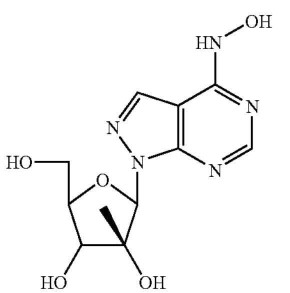 | 1-(2'-C-methyl-β-D-ribofuranosyl)-4-hydroxylamino-pyrazolo[3,4-d]pyrimidine |
| 8 (123) | 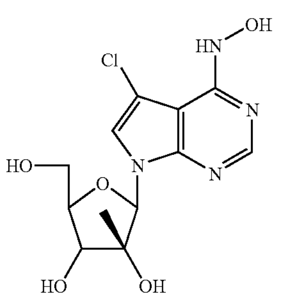 | 7-(2'-C-methyl-β-D-ribofuranosyl)-5-chloro-4-hydroxylamino-pyrrolo[2,3-d]pyrimidine |
| 9 (124) | 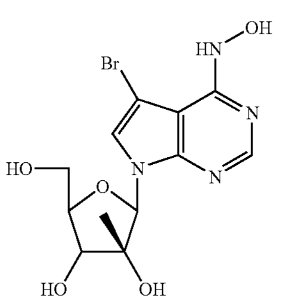 | 7-(2'-C-methyl-β-D-ribofuranosyl)-5-bromo-4-hydroxylamino-pyrrolo[2,3-d]pyrimidine |

-continued

| # | Structure | Name |
|---|---|---|
| 10 (125) | 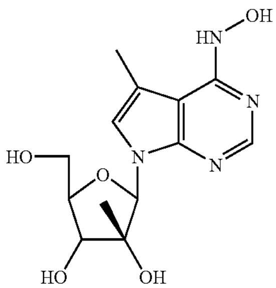 | 7-(2'-C-methyl-β-D-ribofuranosyl)-5-methyl-4-hydroxylamino-pyrrolo[2,3-d]pyrimidine |
| 11 (126) | 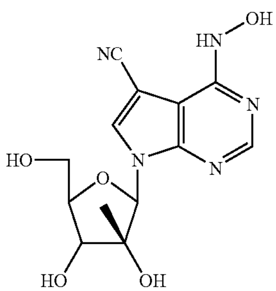 | 7-(2'-C-methyl-β-D-ribofuranosyl)-5-cyano-4-hydroxylamino-pyrrolo[2,3-d]pyrimidine |
| 12 (127) | 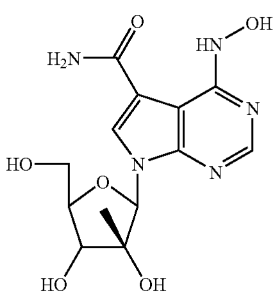 | 7-(2'-C-methyl-β-D-ribofuranosyl)-4-hydroxylamino-pyrrolo[2,3-d]pyrimidine 5-carboxyl amide |
| 13 (128) | 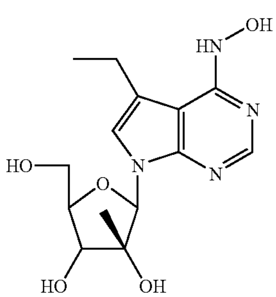 | 7-(2'-C-methyl-β-D-ribofuranosyl)-5-ethyl-4-hydroxylamino-pyrrolo[2,3-d]pyrimidine |
| 14 (129) | 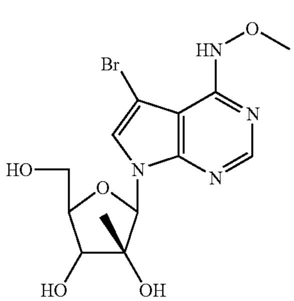 | 7-(2'-C-methyl-β-D-ribofuranosyl)-5-bromo-4-methoxylamino-pyrrolo[2,3-d]pyrimidine |

-continued

| # | Structure | Name |
|---|---|---|
| 15 (130) | 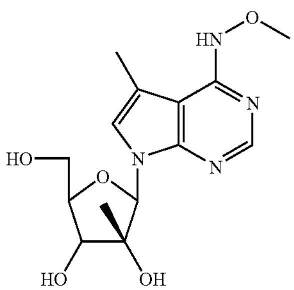 | 7-(2'-C-methyl-β-D-ribofuranosyl)-5-methyl-4-methoxylamino-pyrrolo[2,3-d]pyrimidine |
| 16 (131) | 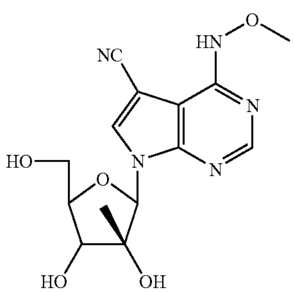 | 7-(2'-C-methyl-β-D-ribofuranosyl)-5-cyano-4-methoxylamino-pyrrolo[2,3-d]pyrimidine |
| 17 (132) | 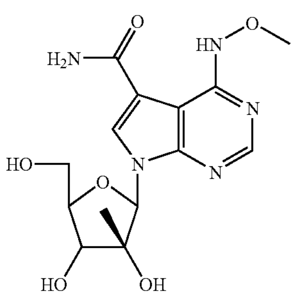 | 7-(2'-C-methyl-β-D-ribofuranosyl)-4-methoxylamino-pyrrolo[2,3-d]pyrimidine 5-carboxyl amide |
| 18 (133) | 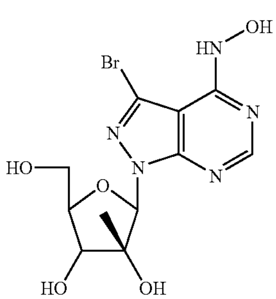 | 1-(2'-C-methyl-β-D-ribofuranosyl)-3-bromo-4-hydroxylamino-pyrazolo[3,4-d]pyrimidine |
| 19 (134) | 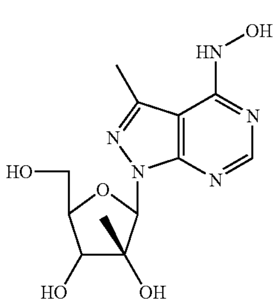 | 1-(2'-C-methyl-β-D-ribofuranosyl)-3-methyl-4-hydroxylamino-pyrazolo[3,4-d]pyrimidine |

-continued

| # | Structure | Name |
|---|---|---|
| 20 (135) | 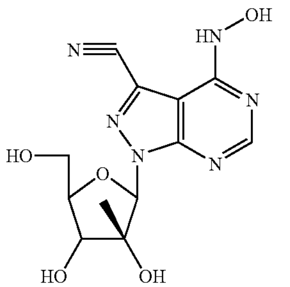 | 1-(2'-C-methyl-β-D-ribofuranosyl)-3-cyano-4-hydroxylamino-pyrazolo[3,4-d]pyrimidine |
| 21 (136) | 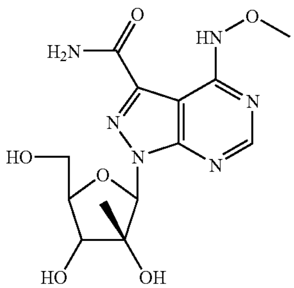 | 1-(2'-C-methyl-β-D-ribofuranosyl)-4-methoxylamino-pyrazolo[3,4-d]pyrimidine-3-carboxamide |
| 22 (137) | 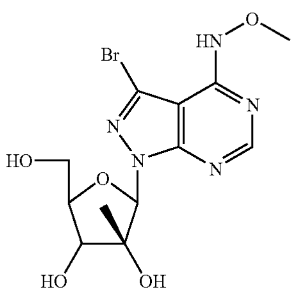 | 1-(2'-C-methyl-β-D-ribofuranosyl)-3-bromo-4-methoxylamino-pyrazolo[3,4-d]pyrimidine |
| 23 (138) | 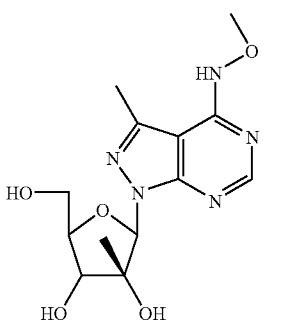 | 1-(2'-C-methyl-β-D-ribofuranosyl)-3-methyl-4-methoxylamino-pyrazolo[3,4-d]pyrimidine |
| 24 (139) | 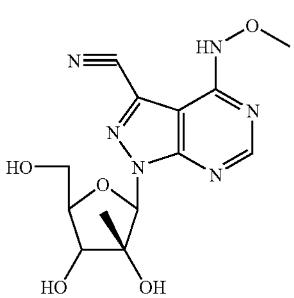 | 1-(2'-C-methyl-β-D-ribofuranosyl)-3-cyano-4-methoxylamino-pyrazolo[3,4-d]pyrimidine |

-continued

| # | Structure | Name |
|---|---|---|
| 25 (140) | 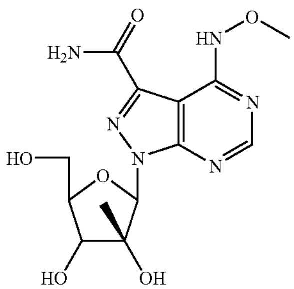 | 1-(2'-C-methyl-β-D-ribofuranosyl)-4-methoxylamino-pyrazolo[3,4-d]pyrimidine-3-carboxamide |
| 26 (226) | 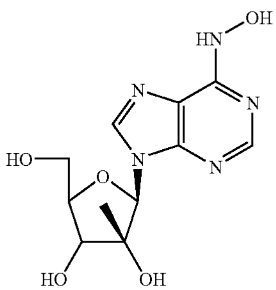 | 9-(2'-C-methyl-β-D-ribofuranosyl)-6-(-S or R-)-hydroxylaminopurine |
| 27 (227) | 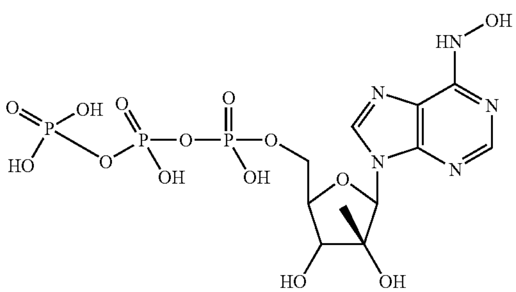 | 9-(2'-C-methyl-5'-O-triphosphate-β-D-ribofuranosyl)-6-(-S or R-)-hydroxylaminopurine |
| 28 (228) | 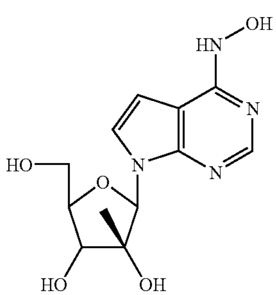 | 7-(β-D-ribofuranosyl)-4-hydroxylamino-pyrrolo[2,3-d]pyrimidine |
| 29 (229) | 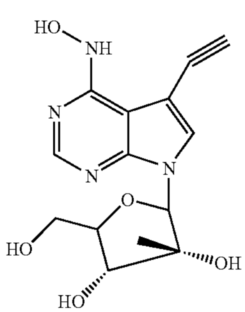 | 7-(2'-C-methyl-β-D-ribofuranosyl)-4-hydroxylamino-5-ethynyl-pyrrolo[2,3-d]pyrimidine |

| # | Structure | Name |
|---|---|---|
| 30 (230) | 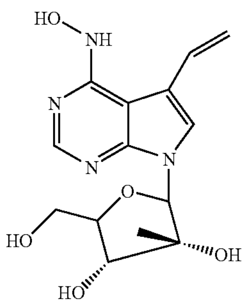 | 7-(2'-C-methyl-β-D-ribofuranosyl)-4-hydroxylamino-5-ethenyl-pyrrolo[2,3-d]pyrimidine |
| 31 (231) | 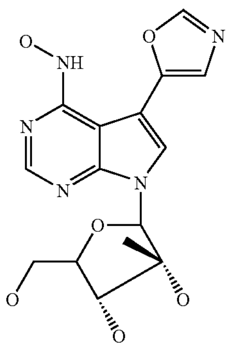 | 7-(2'-C-methyl-β-D-ribofuranosyl)-4-hydroxylamino-5-(1,3-oxazol-5-yl)-pyrrolo[2,3-d]pyrimidine |
| 42 | 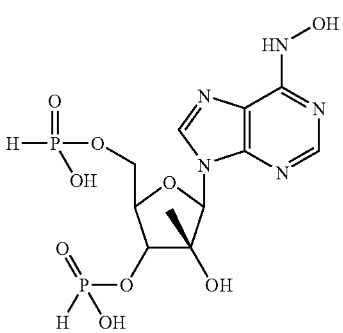 | 6-hydroxylamino-9-(2'-C-methyl-3',5-diphosphite-β-D-ribofuranosyl)purine |
| 32 (25) | 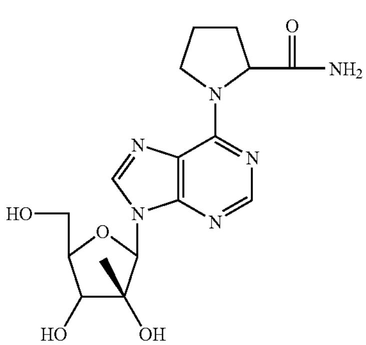 | 9-(2'-C-methyl-β-D-ribofuranosyl)-6-[2-aminocarbonyl-(pyrrolidine-1-yl)]-purine |

| # | Structure | Name |
|---|---|---|
| 33 (33) | 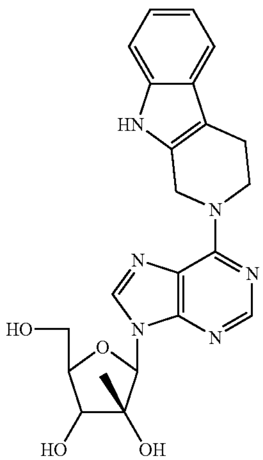 | 9-(2'-C-methyl-β-D-ribofuranosyl)-6-(1,3,4,9-tetrahydro-beta-carbolin-2-yl)purine |
| 34 (57) | 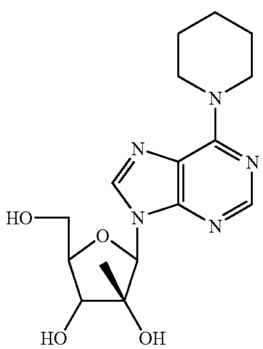 | 9-(2'-C-methyl-β-D-ribofuranosyl)-6-(piperidin-1-yl)purine |
| 35 (64) | 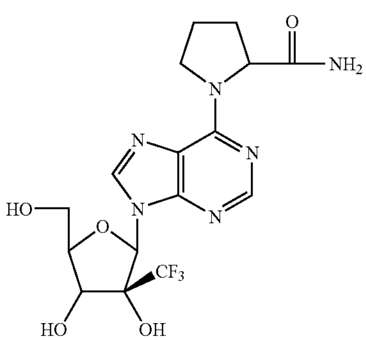 | 9-(2'-C-trifluoromethyl-β-D-ribofuranosyl)-6-[2-aminocarbonyl-(pyrrolidine-1-yl)]-purine |
| 36 (70) | 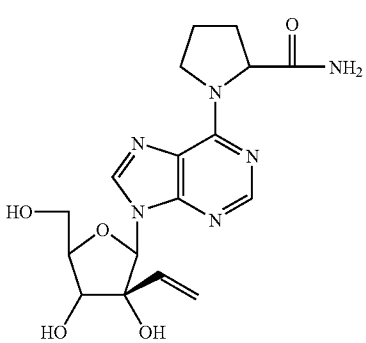 | 9-(2'-C-ethenyl-β-D-ribofuranosyl)-6-[2-aminocarbonyl-(pyrrolidine-1-yl)]-purine |

| # | Structure | Name |
|---|---|---|
| 37 (76) | 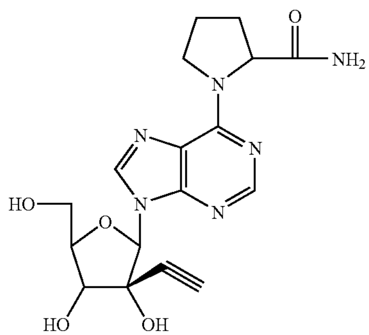 | 9-(2'-C-ethynyl-β-D-ribofuranosyl)-6-[2-aminocarbonyl-(pyrrolidine-1-yl)]-purine |
| 38 (107) | 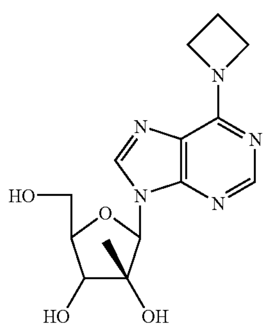 | 9-(2'-C-methyl-β-D-ribofuranosyl)-6-(azetidin-1-yl)purine |
| 39 (108) | 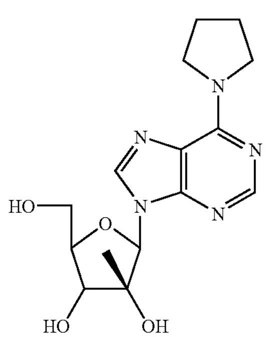 | 9-(2'-C-methyl-β-D-ribofuranosyl)-6-(pyrrolidin-1-yl)purine |
| 40 (113) | 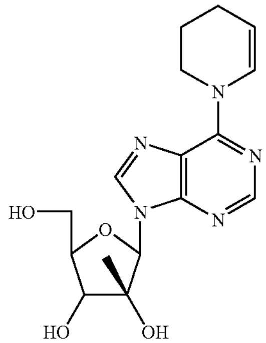 | 9-(2'-C-methyl-β-D-ribofuranosyl)-6-(3,6-dihydro-2H-pyridin-1-yl)purine |

-continued

| # | Structure | Name |
|---|---|---|
| 41 (114) | 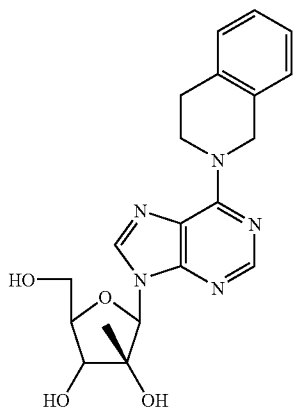 | 9-(2'-C-methyl-β-D-ribofuranosyl)-6-(3,4-dihydro-1H-isoquinolin-2-yl)purine |

This invention is also directed to pharmaceutical compositions comprising a pharmaceutically acceptable diluent and a therapeutically effective amount of a compound of this invention or mixtures of one or more of such compounds.

This invention is still further directed to methods for treating HCV in mammals which methods comprise administering to a mammal diagnosed with HCV or at risk of developing HCV a pharmaceutical composition comprising a pharmaceutically acceptable diluent and a therapeutically effective amount of a compound of this invention or mixtures of one or more of such compounds.

DETAILED DESCRIPTION OF THE INVENTION

The invention is directed to compounds, compositions and methods for treating hepatitis C viral infections. However, prior to describing this invention in detail, the following terms will first be defined:

DEFINITIONS

As used herein, "alkyl" refers to alkyl groups having from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 6 carbon atoms and more preferably 2 to 4 carbon atoms and having at least 1 and preferably from 1-2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl group preferably having from 2 to 6 carbon atoms and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings as defined above for substituted aryl.

"Carboxyl" refers to —COOH or salts thereof.

"Carboxyl esters" refers to the groups —C(O)O-alkyl, —C(O)O-substituted alkyl, —C(O)Oaryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Cycloalkenyl" refers to cyclic alkenyl groups of from 4 to 10 carbon atoms having single or multiple cyclic rings and further having at least 1 and preferably from 1 to 2 internal sites of ethylenic or vinyl (>C=C<) unsaturation.

"Substituted cycloalkyl" and "substituted cycloalkenyl" refers to an cycloalkyl or cycloalkenyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —OP(O)(OH)$_2$ (monophosphate), —OP(O)(OH)OP(O)(OH)$_2$ (diphosphate) and —OP(O)(OH)OP(O)(OH)OP(O)(OH)$_2$ (triphosphate) or salts thereof including partial salts thereof.

"Phosphonate" refers to the groups —OP(O)(R)(OH) or —OP(O)(R)(OR) or salts thereof including partial salts thereof, wherein each R is independently selected from hydrogen, alkyl, substituted alkyl, carboxylic acid, and carboxyl ester.

"Sulfonate ester" refers to the groups —SO$_2$OR where R is selected from the group consisting of alkyl, substituted alkyl, alkenyl, substituted alkenyl, aryl, substituted aryl, heteroaryl, substituted heteroaryl, heterocyclic and substituted heterocyclic.

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid" refers to α-amino acids of the formula H$_2$NCH(R$^7$)COOH where R$^7$ is hydrogen, alkyl, substituted alkyl or aryl. Preferably, the α-amino acid is one of the twenty naturally occurring L amino acids.

The term "carbohydrate" refers to oligosaccharides comprising from 2 to 20 saccharide units. The particular saccharide units employed are not critical and include, by way of example, all natural and synthetic derivatives of glucose, galactose, N-acetylglucosamine, N-acetylgalactosamine, fucose, sialic acid, and the like. In addition to being in their pyranose form, all saccharide units described herein are in their D form except for fucose which is in its L form.

The term "lipid" is an art recognized term defined, for example, by Lehninger, Biochemistry, 1970, at pages 189 et seq. which is incorporated herein by reference in its entirety.

The term "peptide" refers to polymers of α-amino acids comprising from about 2 to about 20 amino acid units, preferably from about 2 to about 10, more preferably from about 2 to about 5.

The term "stabilized phosphate prodrug" refers to mono-, di- and tri-phosphate groups having one or more of the hydroxyl groups pendent thereto converted to an alkoxy, a substituted alkoxy group, an aryloxy or a substituted aryloxy group.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention may be prepared by various methods known in the art of organic chemistry in general and nucleoside and nucleotide analogue synthesis in particular. The starting materials for the syntheses are either readily available from commercial sources or are known or may be prepared by techniques known in the art. General reviews of the preparation of nucleoside and nucleotide analogues are included 1) Michelson A. M. "*The Chemistry of Nucleosides and Nucleotides,*" Academic Press, New York, 1963; 2) Goodman L. "*Basic Principles in Nucleic Acid Chemistry,*" Academic Press, New York, 1974, vol. 1, Ch. 2; and 3) "*Synthetic Procedures in Nucleic Acid Chemistry,*" Eds. Zorbach W. & Tipson R., Wiley, New York, 1973, vol. 1 & 2.

The synthesis of the compounds of this invention generally follows either a convergent or linear synthetic pathway as described below.

The strategies available for synthesis of compounds of this invention include for example:

General Synthesis of 2'-C-Branched Nucleosides
2'-C-Branched ribonucleosides of Formula IV:

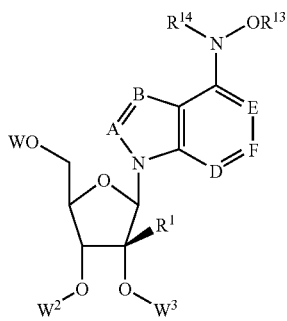

where $R^1$, $R^{13}$, $R^{14}$, W, $W^2$, $W^3$, A, B, D, E and F are as defined above, can be prepared by one of the following general methods.

Convergent Approach: Glycosylation of Nucleobase with Appropriately Modified Sugar The key starting material of this process is an appropriately substituted sugar with 2'-OH and 2'-H with the appropriate leaving group, for example, an acyl group or a chloro, bromo, fluoro or iodo group. The sugar can be purchased or can be prepared by any known means including standard epimerization, substitution, oxidation and/or reduction techniques. For example, commercially available 1,3,5-tri-O-benzoyl-α-D-ribofuranose (Pfanstiel Laboratories, Inc.) can be used. The substituted sugar can then be oxidized with the appropriate oxidizing agent in a compatible solvent at a suitable temperature to yield the 2'-modified sugar. Possible oxidizing agents are, for example, Dess-Martin periodine reagent, $Ac_2O$+ DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetraoxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $R^1$—$SiMe_3$ in TBAF with the ketone with the appropriate non-protic solvent at a suitable temperature, yields the 2'-alkylated sugar. For example, $R^1MgBr/TiCl_4$ or $R^1MgBr/CeCl_3$ can be used as described in Wolfe et al. 1997. *J. Org. Chem.* 62: 1754-1759 (where $R^1$ is as defined herein). The alkylated sugar can be optionally protected with a suitable protecting group, preferably with an acyl, substituted alkyl or silyl group, by methods well known to those skilled in the art, as taught by Greene et al. *Protective Groups in Organic Synthesis*, John Wiley and Sons, Second Edition, 1991.

The optionally protected sugar can then be coupled to the purine base by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

In addition to the above, the 2'- and 3'-C-substituted sugars used in the synthetic methods described herein are well known in the art and are described, for example, by Sommadossi, et al.[5] and by Carrol, et al.[6] both of which are incorporated herein by reference in their entirety.

Scheme 1 below describes the alternative synthesis of a protected sugar that is useful for coupling to the bases described herein.

Scheme 1: Alternative Sugar Synthesis and Coupling

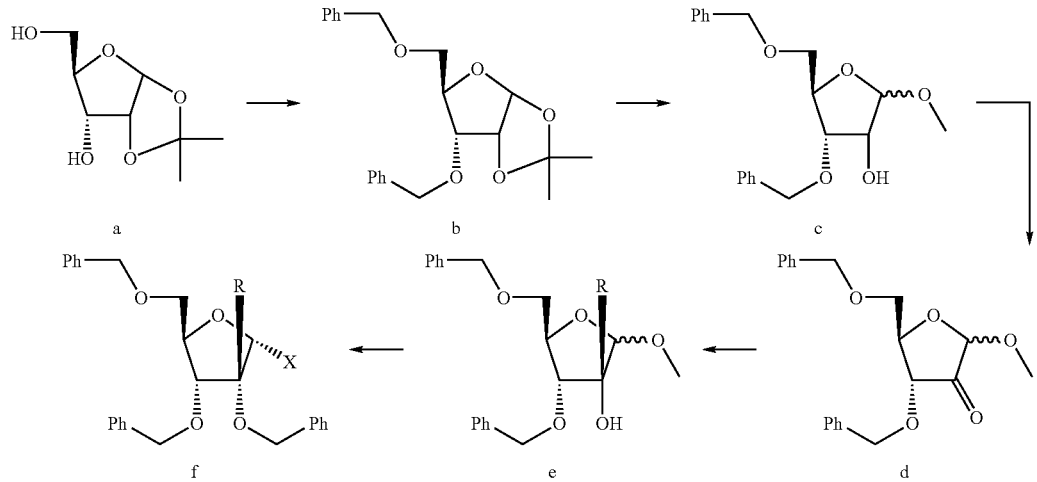

Formation of sugar a in Scheme 1, above, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. R, in sugar e can be hydrogen, alkyl, substituted alkyl, alkenyl, substituted alkenyl, alkynyl, and substituted alkynyl. Particularly preferred R groups are methyl, trifluoromethyl, alkenyl and alkynyl. Sugar e is prepared by using a modification of the Grignard reaction within RMgBr or other appropriate organometallic as described herein (with no titanium/cerium needed). Finally the halogenated sugar used in the subsequent coupling reaction is prepared using the same protection method as used in to make sugar b above. The halogenation is described in Seela.[7]

Subsequently, any of the described nucleosides can be deprotected by methods well known to those skilled in the art, as taught by Greene et al. *Protective Groups in Organic Synthesis,* Jon Wiley and Sons, Second Edition, 1991.

Yet another alternative approach to making protected sugars useful for coupling to heterocyclic bases is detailed in Scheme 2 below. The details for this synthesis can be found in Example 32.

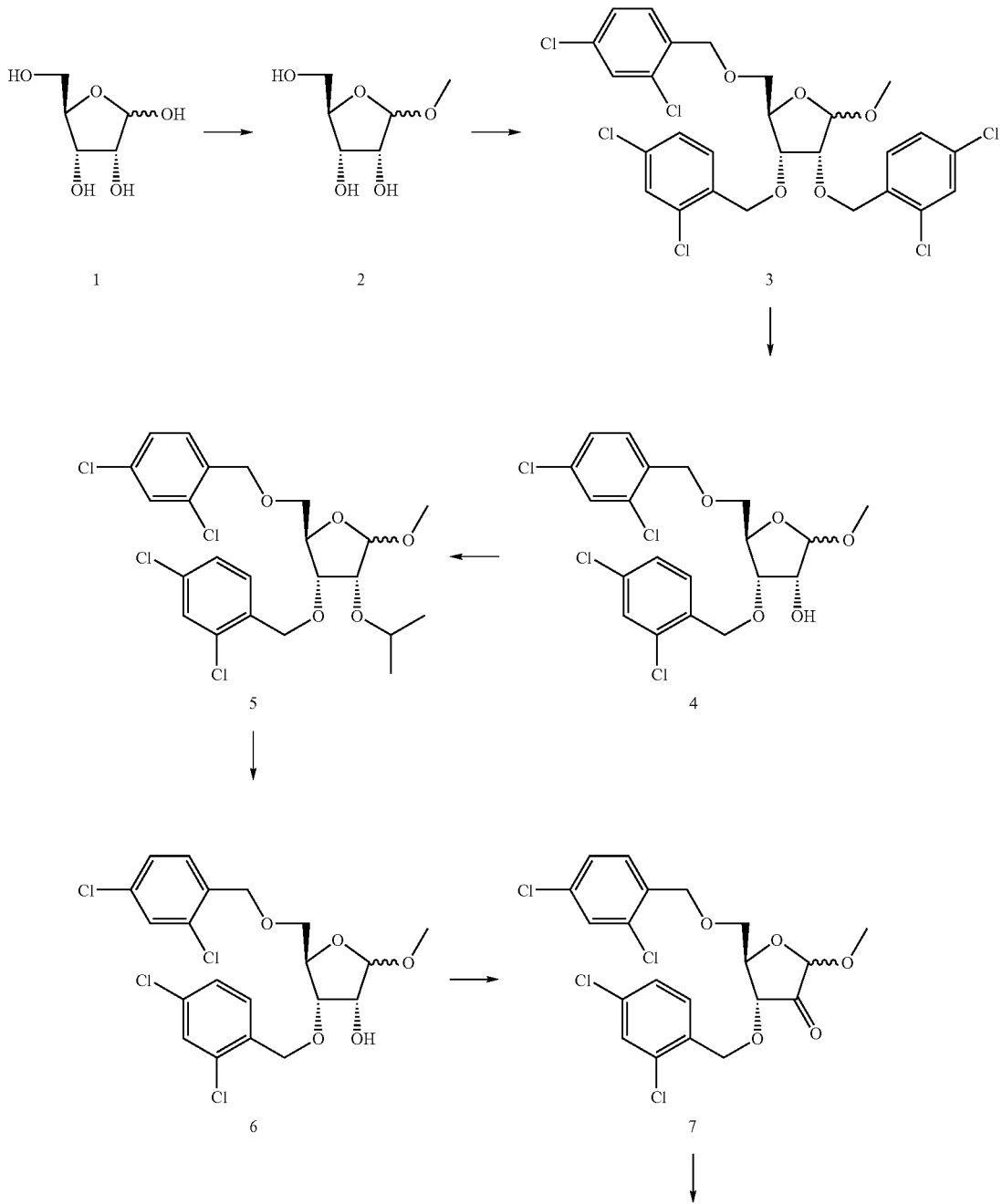

-continued

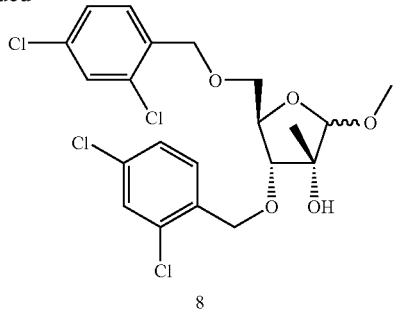

8

Linear Approach Modification of a Pre-Formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are, for example, Dess-Martin periodine reagent, $Ac_2O$+ DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$ ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide. Coupling of an organometallic carbon nucleophile, such as a Grignard reagent, an organolithium, lithium dialkylcopper or $R^1$—$SiMe_3$ in TBAF with the ketone with the appropriate non-protic solvent at a suitable temperature, yields the appropriate substituted nucleoside.

Subsequently, the nucleoside can be deprotected by methods well known to those skilled in the art, as taught by Greene et al. *Protective Groups in Organic Synthesis*, John Wiley and Sons, Second Edition, 1991.

In one embodiment of the invention, the L-enantiomers are preferred. However, D-enantiomers are also useful herein. The L-enantiomers can be corresponding to the compounds of the invention can be prepared following the same foregoing general methods, beginning with the corresponding L-sugar or nucleoside L-enantiomer as starting material. In a particular embodiment, the 2'-C-branched ribonucleoside is desired. In another embodiment, the 3'-C-branched ribonucleoside is desired.

General Synthesis of Heterocyclic Bases
Bases of formula V:

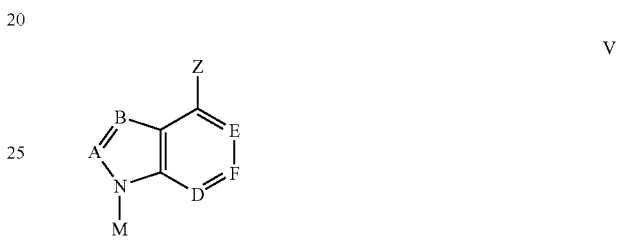

where A, B, D, E, and F are as described above, Z is halo and M is hydrogen or an alkali metal such as lithium are well known in the art and/or can be obtained commercially. See, for example, Carroll, et al., International Patent Application Publication No. WO 02/057425 which application is incorporated by reference herein in its entirety. In addition, the preparation of heterocyclic bases is reviewed by G. Shaw in "*Comprehensive Heterocyclic Chemistry*," Pergamon Press, Vol. 5, chapter 4.09, p. 449 and "*Comprehensive Heterocyclic Chemistry II*" Pergamon Press, Vol. 7, chapter 7.11, p. 397.

For example, the appropriate heterocyclic base of Formula V may be prepared from the heterocyclic base wherein the 2 or 8 position of the heterocyclic base is substituted with a suitable leaving group such as halogen or sulphonate. Such heterocyclic base precursors bearing leaving groups are available commercially, e.g. 6-chloropurine (Aldrich Chemical Company), 2,6-dichloropurine (Aldrich Chemical Company), 2-chloro-6-aminopurine (Aldrich Chemical Company), 8-bromoadenine (Sigma-Aldrich Company Limited) or obtained by procedures known in the art. For example 2- and 6-chloro substituted purines can be prepared by chlorination of the corresponding 2 and 6-hydroxypurines respectively by the use of chlorinating agents such as phosphorus oxychloride (Bakuni et al. *Indian J. Chem.*, Sect B 1984, 23, 1286; LaMontagne et al. *J. Heterocycl. Chem.* 1983, 20, 295) while introduction of a bromine into the 8-position of purines can be accomplished by direct bromination using brominating agents such as, for example, bromine (Mano et al, *Chem Pharm Bull* 1983, 31, 3454) or N-bromosuccinimide (Kelley et al. *Heterocycl. Chem.* 1990, 27, 1505). The purines where the 6-substituent is hydroxylamino, alkoxylamino may be prepared by treatment of the corresponding 6-halopurine with the appropriate hydroxylamines and alkoxylamines, (for example, Chae et al. *J Med Chem,* 1994, 37, 342; Niebch and Schneider, Z. Naturforsch. B. Anorg. *Chem. Org. Chem. Biochem. Biophys. Biol.* 1972, 27, 675; LaMontagne et al., *Heterocycl Chem* 1983, 20, 295; Estep et al *J Med Chem* 1995, 38, 2582). Similarly, 2-substituted purines can be prepared from the corresponding 2-halopurine, for example, purines where the 2-substituent is alkoxy, aryloxy, SH, alkythio, arylthio or $NR^3R^4$ can be prepared from the corresponding 2-halopurine by treatment with alkoxides, thiols or amines (e.g. Barlin and Fenn, *Aust J Chem,* 1983, 36, 633; Nugiel et al., *J Org Chem,* 1997, 62, 201). Similarly, 8-substituted purines can be prepared from the corresponding 8-halopurines. For example purines where the 8-substituent is alkoxy, aryloxy, SH, alkythio, arylthio or $NR^3R^4$ can be prepared by treatment of the corresponding 8-bromopurine with the appropriate alkoxides, thiols or amines (Xing et al, *Tetrahedron Lett,* 1990, 31, 5849; Mano et al, *Chem Pharm Bull* 1983, 31, 3454).

In some cases where the 6-substituent is a nitrogen containing heteroaryl or heterocyclic group linked through the nitrogen atom attached to the purine ring which may be prepared from the 6-aminopurine by reaction with a dicarbonyl compound or a reactive derivative of this such as an acetal. For example, 6-(1H-pyrrol-1-yl)-1H-purine can be prepared from a 6-aminopurine by reaction with 2,5-dimethoxytetrahydrofuran as described by Estep et al *J Med Chem* 1995, 38, 2582.

General Synthesis of N6-Substituted Adenine and N4-Substituted Cytosine

Synthesis of 6-hydroxamino or alkoxyamino-substituted purines is shown in Scheme 3. Synthesis of 9-(2'-C-methyl-β-D-ribofuranosyl)-6-methylthio-purine 49, is performed as described by R. Harry-O'kuru, J. Smith, and M. Wolf *J. Org. Chem.* 1997, 62, 1754-1759. Methylthio-purine is oxidized to methylsulfonyl-purine, 51, using the procedure described by Y-Z. Xu *Tetrahedron,* 1996, 52, 10737-10750; Y-Z. Xu, Q. Zheng, and P. Swann *Nucleosides Nucleotides* 1995, 14, 929-934. For substitution of methylsulfonyl for hydroxylamino or alkoxyamino, protocols similar to the protocol reported for deoxynucleosides by P. Srivastava, G. Revankar, R. Robins, and R. Rousseau *J. Med. Chem.,* 1981, 24, 393-398, can be used and provide for the N-hydroxy or N-alkoxy derivative, 52, where $R^{13}$ is as described above. Bromination of purine nucleosides can be performed as described by J. Gerster et al. *J. Org. Chem.* 1968, 33, 1070-1073.

Scheme 3

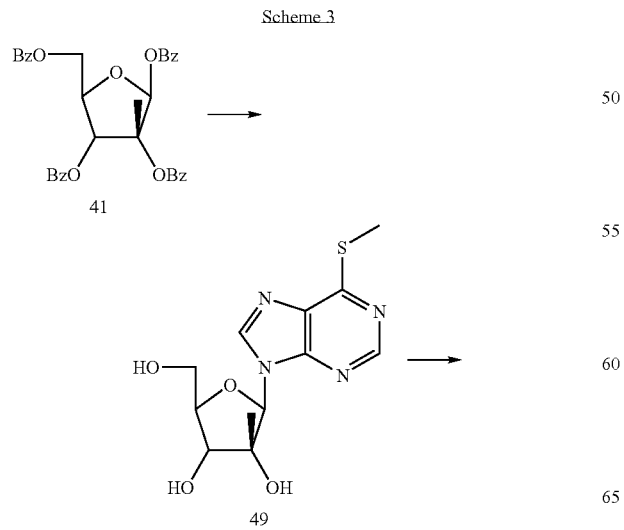

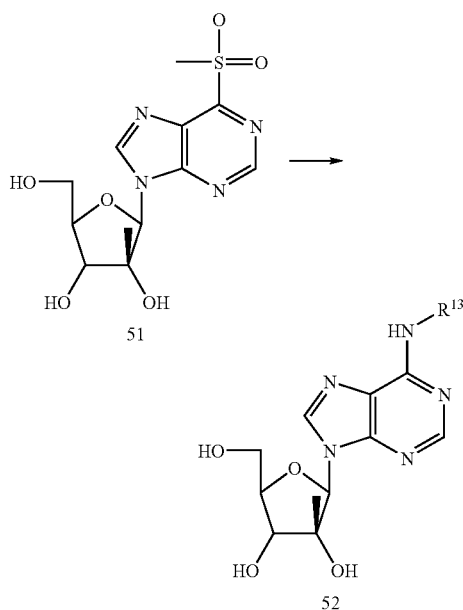

Synthesis of 4-hydroxylamino- and 4-methoxy-lamino-derivatives of 7-(2'-C-methyl-β-D-ribofuranosyl)-pyrrolo[2,3-d]pyrimidines and 1-(2'-C-methyl-β-D-ribofuranosyl)-pyrazolo[3,4-d]pyrimidines The synthesis of 4-hydroxylamino- and 4-methoxylamino-derivatives of 7-(2'-C-methyl-β-D-ribofuranosyl)-pyrrolo[2,3-d]pyrimidines is shown in Scheme 4 through Scheme 7.

Scheme 4

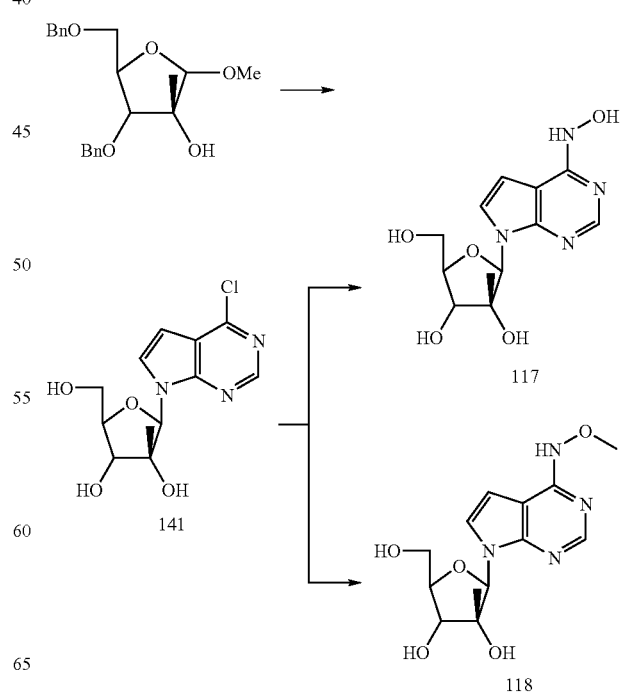

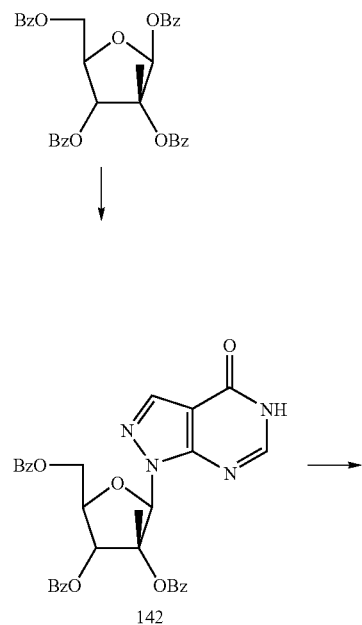
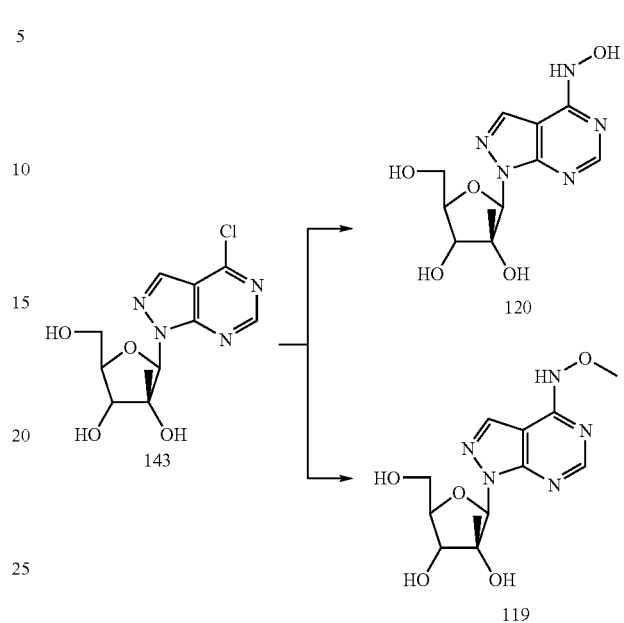
Scheme 5
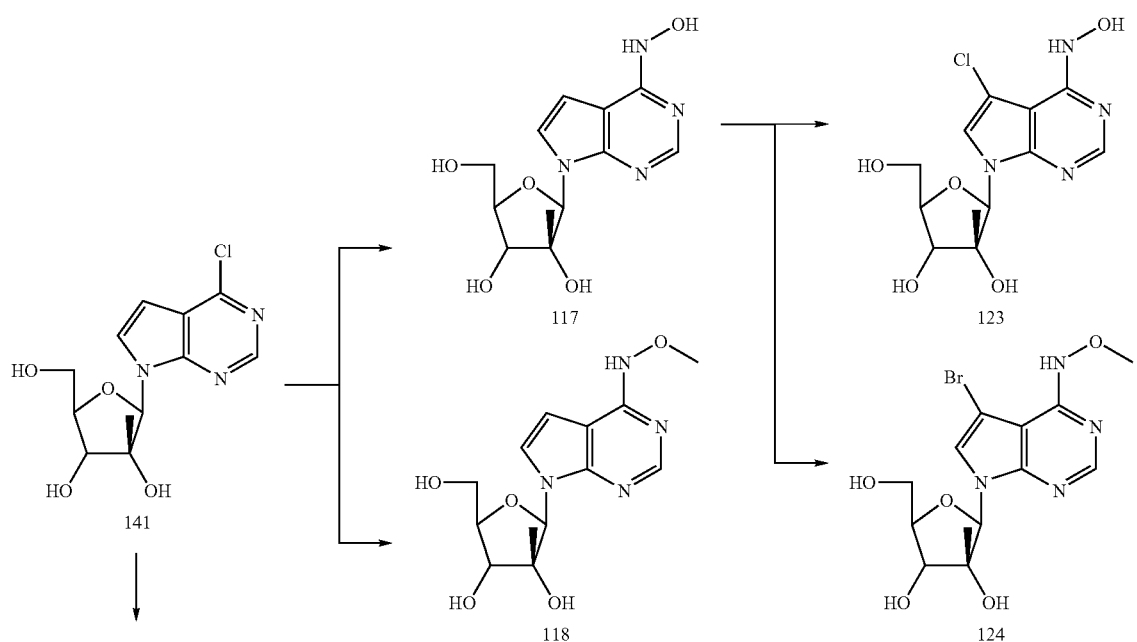

-continued
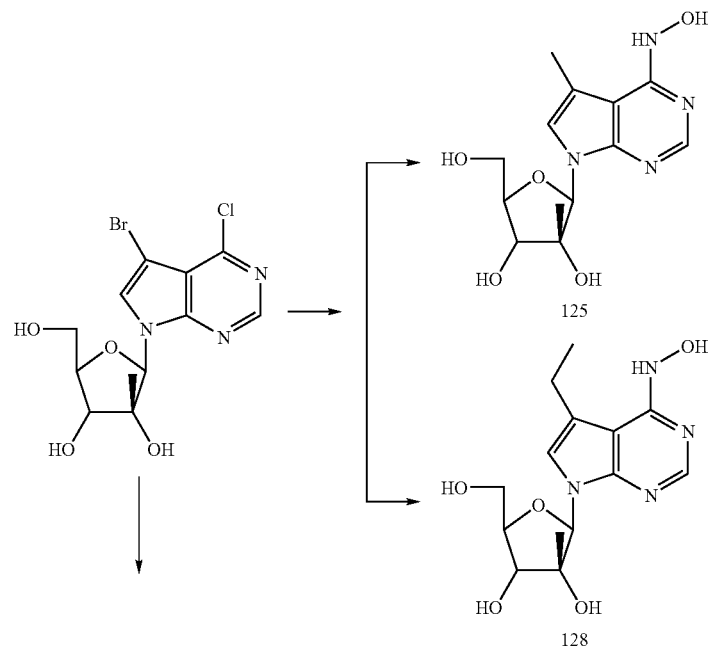
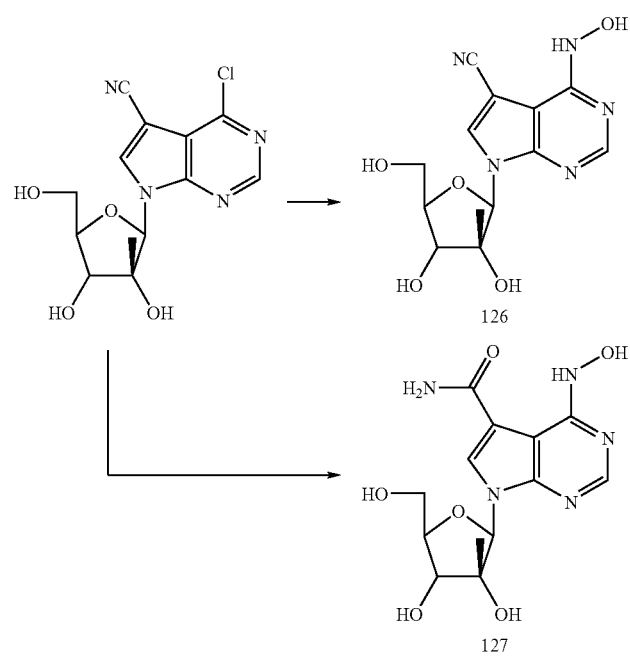

Scheme 6
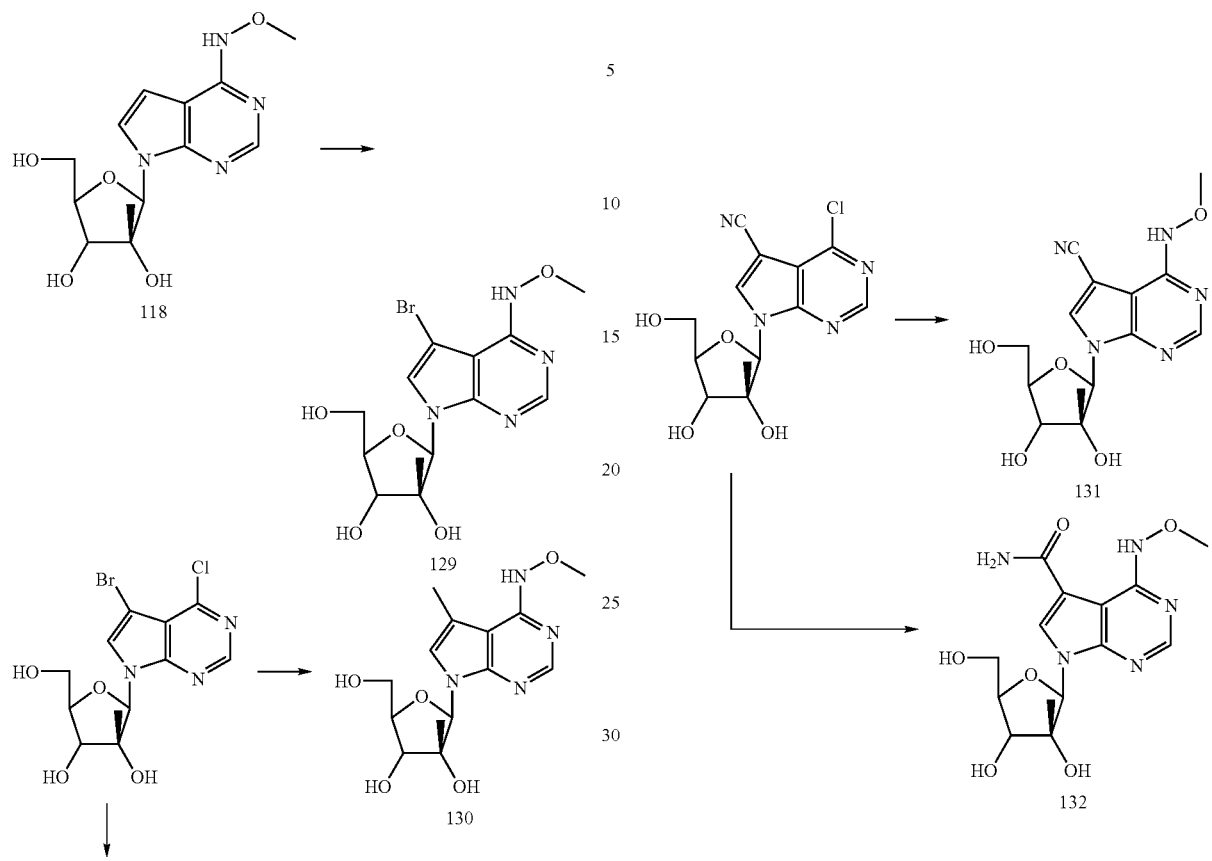
Scheme 7
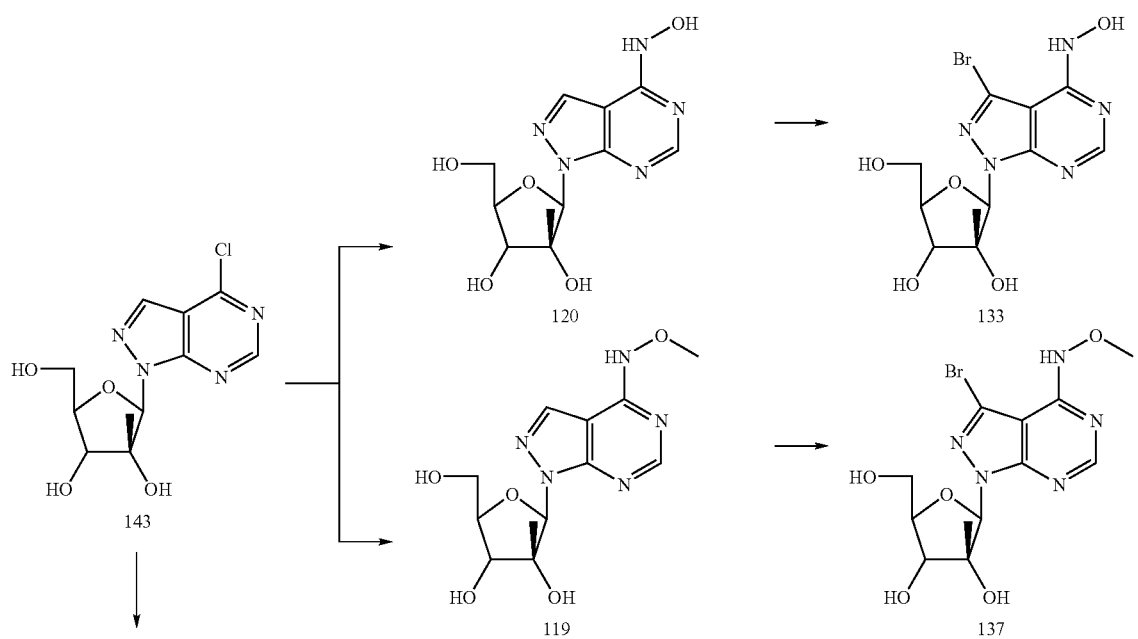

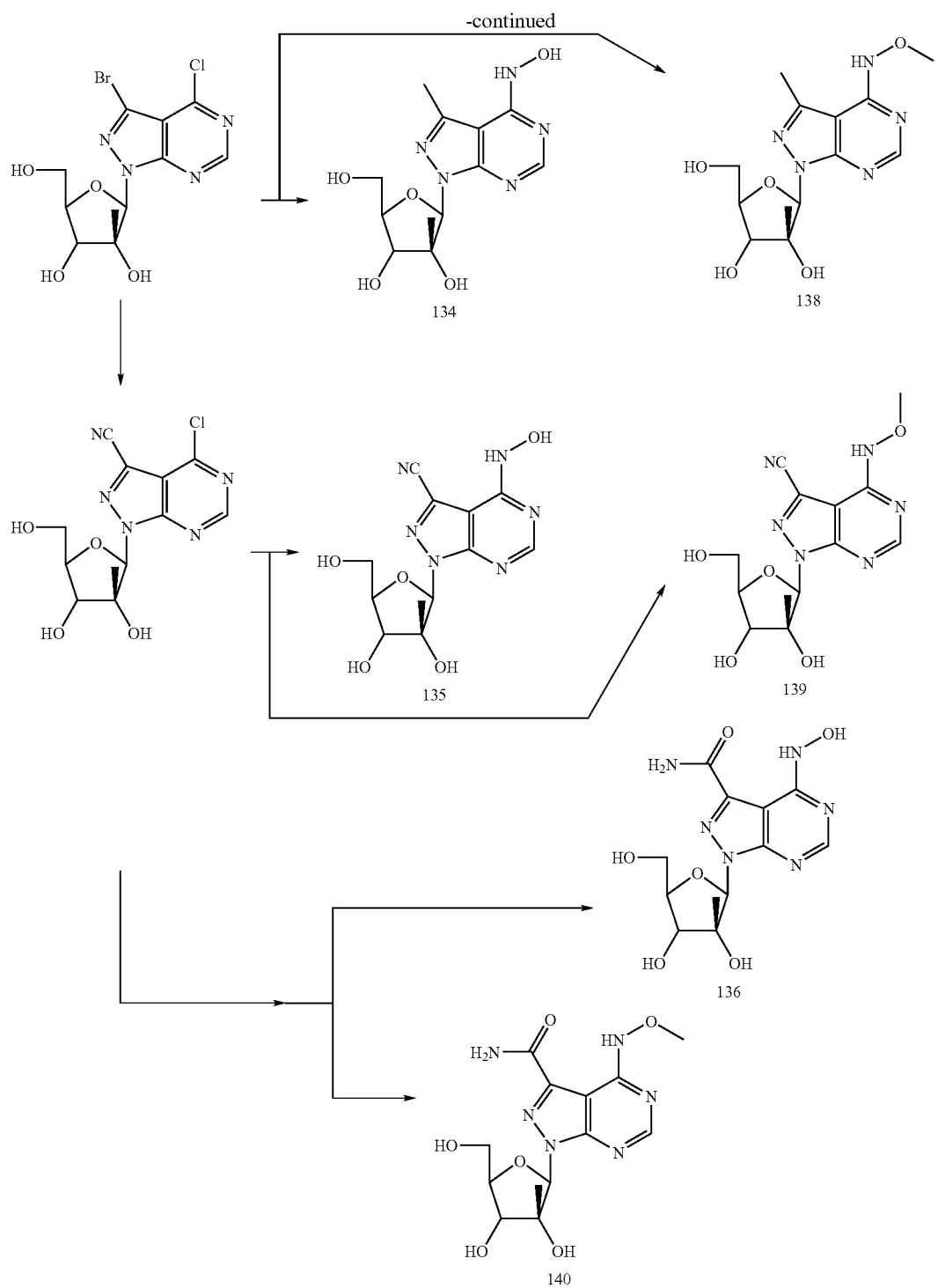

7-(2'-C-methyl-β-D-ribofuranosyl)-4-chloro-pyrrolo[2,3-d]pyrimidine (141) can be prepared as described in WO 02/057287, p 27-30. 7-(2'-C-methyl-β-D-ribofuranosyl)-4-hydroxylamino-pyrrolo[2,3-d]pyrimidine (117) was prepared from nucleoside 141 by reaction with hydroxylamine (prepared as described by P. K. Chang, J. Med. Chem., 1965, 8, 884).

7-(2'-C-methyl-β-D-ribofuranosyl)-4-methoxylamino-pyrrolo[2,3-d]pyrimidine (118) can be prepared from the nucleoside 141 substituting methoxylamine for hydroxylamine.

2,3,5-tri-O-benzoyl-2'-methyl-1,5-dihydro-pyrazolo[3,4-d]pyrimidin-4-one (142) can be synthesized by substitution of 6-bromopurine for 1,5-dihydro-pyrazolo[3,4-d]pyrimidin-4-one.

2,3,5-tri-O-benzoyl-2'-methyl-4-chloro-pyrazolo[3,4-d]pyrimidine (143) can be obtained from nucleoside 142 by reaction with SOCl$_2$.

Nucleoside 143 can be transformed to 1-(2'-C-methyl-β-D-ribofuranosyl)-4-hydroxylamino-pyrazolo[3,4-d]pyrimidine (120) by reaction with hydroxylamine (prepared as described by P. K. Chang, J. Med. Chem., 1965, 8, 884).

1-(2'-C-methyl-β-D-ribofuranosyl)-4-methoxylamino-pyrazolo[3,4-d]pyrimidine (119) can be prepared from the nucleoside 143 substituting hydroxylamine for methoxylamine.

7-(2'-C-methyl-β-D-ribofuranosyl)-5-chloro-4-hydroxylamino-pyrrolo[2,3-d]pyrimidine (123) can be prepared from nucleoside 117 by reaction with N-chlorosuccinimide (NCS).

7-(2'-C-methyl-β-D-ribofuranosyl)-5-bromo-4-hydroxylamino-pyrrolo[2,3-d]pyrimidine (124) can be prepared from nucleoside 117 by reaction with N-bromosuccinimide (NBS).

7-(2'-C-methyl-β-D-ribofuranosyl)-5-methyl-4-hydroxylamino-pyrrolo[2,3-d]pyrimidine (125) can be prepared from nucleoside 141 in three steps (1) reacting nucleoside 141 with NBS affording the 7-bromo-6-chloro-7-deazapurine riboside; (2) reacting the nucleoside from Step 1 with palladium tetrakis(triphenylphosphine) and trimethylboroxine affording the 7-methyl-6-chloro-7-deazapurine riboside; (3) reacting the nucleoside from Step 2 with hydroxylamine.

7-(2'-C-methyl-β-D-ribofuranosyl)-5-methyl-4-methoxylamino-pyrrolo[2,3-d]pyrimidine (130) can be synthesized substituting methoxylamine for hydroxylamine.

7-(2'-C-methyl-β-D-ribofuranosyl)-5-ethyl-4-hydroxylamino-pyrrolo[2,3-d]pyrimidine (128) can be prepared by reaction of the 7-bromo-6-chloro-7-deazapurine riboside with palladium tetrakis(triphenylphosphine) and diethyl zinc affording the 7-ethyl-6-chloro-7-deazapurine riboside and subsequent reaction of the 7-ethyl-6-chloro-7-deazapurine riboside with hydroxylamine.

7-(2'-C-methyl-β-D-ribofuranosyl)-5-cyano-4-hydroxylamino-pyrrolo[2,3-d]pyrimidine (126) can be prepared by reaction of the 7-bromo-6-chloro-7-deazapurine riboside with palladium tetrakis(triphenylphosphine) and zinc cyanide affording the 7-cyano-6-chloro-7-deazapurine riboside and subsequent reaction of the 7-cyano-6-chloro-7-deazapurine riboside with hydroxylamine.

7-(2'-C-methyl-β-D-ribofuranosyl)-5-cyano-4-methoxylamino-pyrrolo[2,3-d]pyrimidine (131) can be synthesized substituting methoxylamine for hydroxylamine.

7-(2'-C-methyl-β-D-ribofuranosyl)-4-hydroxylamino-pyrrolo[2,3-d]pyrimidine 5-carboxylamide (127) can be prepared by converting the 7-cyano-6-chloro-7-deazapurine riboside into the 7-carboxamide-6-chloro-7-deazapurine and subsequent reaction of the 7-carboxamide-6-chloro-7-deazapurine with hydroxylamine.

7-(2'-C-methyl-β-D-ribofuranosyl)-4-methoxylamino-pyrrolo[2,3-d]pyrimidine 5-carboxylamide (132) can be synthesized substituting methoxylamine for hydroxylamine.

7-(2'-C-methyl-β-D-ribofuranosyl)-5-bromo-4-methoxylamino-pyrrolo[2,3-d]pyrimidine (129) can be prepared from nucleoside 118 by reaction with N-bromosuccinimide (NBS).

1-(2'-C-methyl-β-D-ribofuranosyl)-3-bromo-4-hydroxylamino-pyrazolo[3,4-d]pyrimidine (133) can be prepared from nucleoside 120 by reaction with N-bromosuccinimide (NBS).

1-(2'-C-methyl-β-D-ribofuranosyl)-3-methyl-4-hydroxylamino-pyrazolo[3,4-d]pyrimidine (134) can be prepared from nucleoside 143 in three steps (1) reacting nucleoside 143 with NBS; (2) reacting the nucleoside from Step 1 with palladium tetrakis(triphenylphosphine) and trimethylboroxine; (3) reacting the nucleoside from Step 2 with hydroxylamine.

1-(2'-C-methyl-β-D-ribofuranosyl)-3-cyano-4-hydroxylamino-pyrazolo[3,4-d]pyrimidine (135) can be synthesized from nucleoside 143 using conditions described for synthesis of compound 126.

1-(2'-C-methyl-β-D-ribofuranosyl)-4-hydroxylamino-pyrazolo[3,4-d]pyrimidine-3-carboxamide (136) can be synthesized from nucleoside 143 using conditions described for synthesis of compound 127.

1-(2'-C-methyl-β-D-ribofuranosyl)-3-bromo-4-methoxylamino-pyrazolo[3,4-d]pyrimidine (137) can be prepared from nucleoside 119 using conditions described for synthesis of compound 125.

1-(2'-C-methyl-β-D-ribofuranosyl)-3-methyl-4-methoxylamino-pyrazolo[3,4-d]pyrimidine (138) can be synthesized from nucleoside 143 using conditions described for synthesis of compound 125, substituting methoxylamine for hydroxylamine.

1-(2'-C-methyl-β-D-ribofuranosyl)-3-cyano-4-methoxylamino-pyrazolo[3,4-d]pyrimidine (139) can be synthesized from nucleoside 143 using conditions described for synthesis of compound 126, substituting methoxylamine for hydroxylamine.

1-(2'-C-methyl-β-D-ribofuranosyl)-4-methoxylamino-pyrazolo[3,4-d]pyrimidine-3-carboxamide (140) can be synthesized from nucleoside 143 using conditions described for synthesis of compound 127, substituting methoxylamine for hydroxylamine.

Following procedures set forth above and procedures well-known in the art, as well as those described by Li et al.[8], 2'-C-trifluoromethyl-β-D-ribofuranosyl derivatives can be prepared.

By following the procedures set forth above, as well as procedures well known in the art, including those procedures set forth by Devos[4], et al. and Sommadossi[5] et al., the following compounds can be made.

1-Deazapurines can be prepared and coupled to ribofuranosyl derivatives as described in by Cristalli, et al. in *J. Med. Chem.*, 1987, 30(9) p. 1686 or Seela, F., et al. in *Nucleosides Nucleotides*, 1998, 17(4), p. 729.

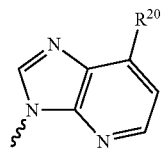

R$^{20}$ is a suitable leaving such as chloro or bromo.

Utility, Testing, and Administration

Utility

The present invention provides novel compounds possessing antiviral activity, including hepatitis C virus. The compounds of this invention inhibit HCV replication by inhibiting the enzymes involved in replication, including RNA dependent RNA polymerase. They may also inhibit other enzymes utilized in the activity or proliferation of HCV.

The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention maybe used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of this invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract, in particular for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this invention or a mixture thereof in combination with at least one pharmaceutically acceptable excipient. Acceptable excipients are non-toxic, aid administration, and do not adversely affect the therapeutic benefit of the compound of this invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %. Representative pharmaceutical formulations containing a compound of this invention are described below.

EXAMPLES

The examples below as well as throughout the application, the following abbreviations have the following meanings. If not defined, the terms have their generally accepted meanings.

| | |
|---|---|
| AcOH or HOAc = | acetic acid |
| Ac$_2$O | acetic anhydride |
| atm = | atmosphere |
| CAN = | ceric ammonium nitrate |
| cm = | centimeter |
| d = | doublet |
| dd = | doublet of doublets |
| dt = | doublet of triplets |
| DCB = | dichlorobenzyl |
| DCC = | N,N-dicyclohexyl carbodiamide |
| DCM = | dichloromethane |
| DMAP = | dimethylaminopyridine |
| DMEM = | Delbecco's minimum eagles medium |
| DMF = | N,N-dimethylformamide |
| DMSO = | dimethylsulfoxide |
| DTT = | dithiothreitol |
| EDTA = | ethylene diamine tetraacetic acid |
| eq. = | equivalents |
| ether = | diethyl ether |

-continued

| | |
|---|---|
| g = | gram |
| h = | hour |
| HCV = | hepatitis C virus |
| HPLC = | high performance liquid chromatography |
| IE HPLC = | Ion Exchange high performance liquid chromatography |
| IPTG = | |
| IU = | international units |
| kb = | kilobase |
| kg = | kilogram |
| m = | multiplet |
| M = | molar |
| Me = | methyl |
| MeOH = | methanol |
| mg = | milligram |
| mL = | milliliter |
| mm = | millimeters |
| mM = | millimolar |
| mmol = | millimol |
| MS = | mass spectrum |
| NBS = | n-bromosuccinimide |
| NCS = | n-chlorosuccinimide |
| ng = | nanograms |
| nm = | nanometers |
| nM = | nanomolar |
| NMR = | nuclear magnetic resonance |
| NTA = | nitrilotriacetic acid |
| NTP = | nucleotide triphosphate |
| RP HPLC = | reverse phase high performance liquid chromatography |
| s = | singlet |
| t = | triplet |
| TBAF = | tetrabutylammonium fluoride |
| THF = | tetrahydrofuran |
| µL = | microliters |
| v/v = | volume to volume |
| w/w = | weight to weight |
| wt % = | weight percent |

In addition, all reaction temperatures are in degrees Celcius unless reported otherwise and all percentages are molar percents again unless indicated otherwise.

Example 1

6-hydroxylamino-9-(2'-C-methyl-β-D-ribofuranosyl)purine and 6-hydroxylamino-9-(2'-C-methyl-α-D-ribofuranosyl)purine Step 1. Synthesis of 6-chloro-9-[2'-C-methyl-3',5'-bis-O-(2,4-dichlorophenyl methyl)-β-D-ribofuranosyl]purine

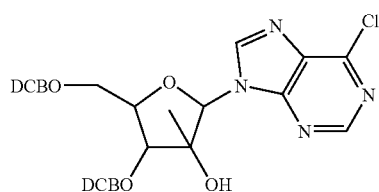

6-Chloropurine (6 g, 38 mmol) was suspended in 1 L of dry acetonitrile. 1.5 g of NaH (60% in oil) was added and the mixture was stirred for 4 hours under an argon atmosphere. 1-O-Methyl-3,5-bis-O-(2,4-dichlorophenylmethyl)-2'-C-methyl-β-D-ribofuranoside (7 g, 14 mmol) was dissolved in 200 mL of dry dichloromethane, cooled to 0° C. and HBr/AcOH was added drop wise. The reaction was kept for 1 hour at 0° C. and 3 hours more at ambient temperature. The solvent was then evaporated. The mixture was 2 times co-evaporated with dry toluene, dissolved in 200 mL of dry dichloromethane and added to the sodium salt of the base. The reaction mixture was kept at room temperature over night and evaporated to dryness. The residue was distributed between ethyl acetate and water. Water fraction was extracted with ethyl acetate (4×100 mL), combined organic fractions washed with brine, dried over sodium sulfate then evaporated. The residue was purified by flash chromatography on silica gel (ethyl acetate/toluene 3:7 v/v) to yield 5.5 g (68%) of protected nucleoside.

MS: 525.07 (M+NH$_4^+$).

Step 2. Synthesis of 6-chloro-9-(2'-C-methyl-β-D-ribofuranosyl)purine and 6-chloro-9-(2'-C-methyl-α-D-ribofuranosyl)purine

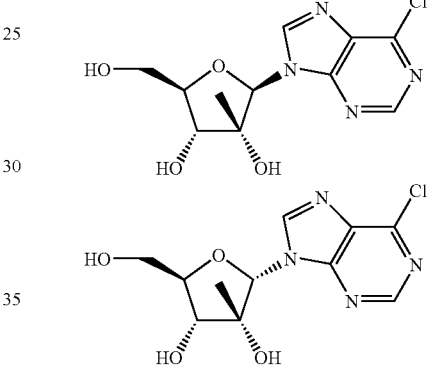

The solution of the product from Step 1 (4.8 g, 10 mmol) was dissolved in dichloromethane (200 mL) and then cooled to –78° C. To the cooled solution was added boron trichloride (1 M in dichloromethane) (100 mL, 100 mmol). The mixture was stirred at –78° C. for 1 hour, then at –20° C. for several hours. The reaction was quenched with dichloromethane/methanol 1:1 (100 mL), stirred at –20° C. for 0.5 hour and neutralized at 0° C. with aqueous ammonia. The solid was filtered, washed with dichloromethane/methanol 1:1 and the combined extracts evaporated in vacuo. The residue was purified on silica gel column with chloroform/methanol as eluent. Corresponding fractions were combined, concentrated and recrystallized from methanol/ether to yield 1.6 g (70%) of the title compound.

MS: 301.93 (M+H); H$^1$-NMR (DMSO-d6): 0.90 (s, 3H, 2'-CH$_3$), 3.80-5.00 (m, sugar & water), 5.35-5.37 (d, 1H, H-3'), 5.45 (s, 1H, OH), 6.05 (s, 1H, H-1'), 8.81 & 9.03 (s, 2H, purine).

The mother liquid was repurified by column chromatography to isolate 150 mg (10%) of 6-chloro-9-(2'-C-methyl-α-D-ribofuranosyl)purine. MS: 301.93 (M+H); H$^1$-NMR (DMSO-d6): 0.90 (s, 3H, 2'-CH$_3$), 3.98-5.00 (m, sugar & water), 5.42-5.36 (t, 1H, OH), 5.45 (s, 1H, H-3'), 6.40 (s, 1H, H-1'), 8.76 & 9.36 (s, 2H, purine).

Step 3. Synthesis of 6-hydroxylamino-9-(2'-C-methyl-β-D-ribofuranosyl)purine and 6-hydroxylamino-9-(2'-C-methyl-α-D-ribofuranosyl)purine

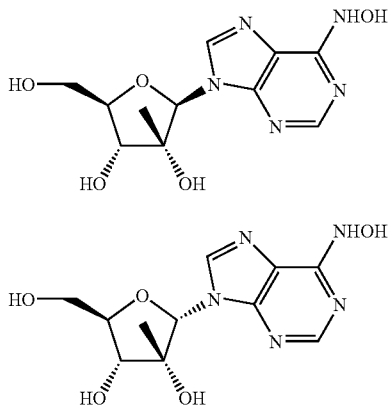

6-Chloro-9-(2'-C-methyl-β-D-ribofuranosyl)purine (300 mg, 1 mmol) was suspended in 30 mL of dry ethanol and O-trimethylsilyl hydroxylamine (10 mmol) was added. The mixture was refluxed for 2 hours, evaporated and the crude mixture was separated by RP HPLC on a Phenominex column (250×20 mm) using a gradient of acetonitrile in water of from 0 to 100%. Corresponding fractions were evaporated to yield 200 mg (70%) of the beta isomer, Nucleoside A,3 as off-white foam. MS: 298.17 (M+H); H$^1$-NMR (DMSO-d6): 0.84 (s, 3H, 2'-CH$_3$), 3.82-4.20 (m, sugar & water), 4.83-4.96 (m, 2H, OH & H-3'), 6.05 (s, 1H, H-1'), 8.05 & 9.53 (s, 2H, purine).

Nucleoside B was obtained from corresponding α-anomer of 6-chloropurine nucleoside from Step 2. MS: 298.13 (M+H); H$^1$-NMR (DMSO-d6): 1.01 (s, 3H, 2'-CH$_3$), 3.42-3.82 (m, sugar), 4.50 (t, 1H, OH), 4.97 (m, 1H, H-3'), 5.32 (t, 1H, OH), 6.16 (s, 1H, H-1'), 8.40 & 9.93 (s, 2H, purine), 11.03 (s, 1H, NHOH).

Example 2

9-(2'-C-methyl-β-D-ribofuranosyl)-6-methoxyaminopurine (111)

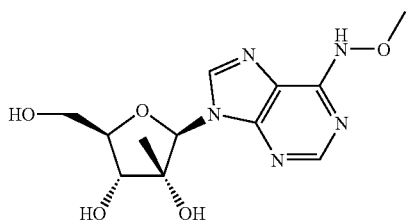

The above compound was synthesized from methoxylamine and 6-chloro-9-(2'-C-methyl-β-D-ribofuranosyl)purine as described in Example 1, Step 3.

MS 312.41 (M+H). H$^1$-NMR (DMSO-d6): 0.89 (s, 3H, CH$_3$), 3.80-4.00 (m, 10H, sugar+OCH3), 5.00-5.20 (3H, sugar), 5.79 (s, 1H, H-1'), 7.88 & 8.21 (s, 1H, purine).

Example 3

7-(2'-C-methyl-β-D-ribofuranosyl)-4-hydroxylamino-pyrrolo[2,3-d]pyrimidine (117)

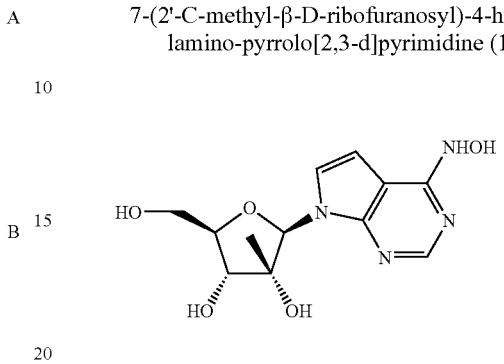

Step 1. Synthesis of 7-(2'-C-methyl-β-D-ribofuranosyl)-4-chloro-pyrrolo[2,3-d]pyrimidine (141) was prepared as described in WO 02/057287, p 27-30

Step 2. 7-(2'-C-methyl-β-D-ribofuranosyl)-4-hydroxylamino-pyrrolo[2,3-d]pyrimidine (117)

Nucleoside 141 (300 mg, 1 mM) was dissolved in dry ethanol (10 mL). A solution of hydroxylamine (prepared as described by P. K. Chang, J. Med. Chem., 1965, 8, 884) was added (10 mM) and the mixture was refluxed for 1 h and then concentrated in vacuo. The residue was purified by HPLC 0-30% of buffer B in buffer A, 30 minutes, flow 10 mL/minutes.

A—0.2% triethylammonium acetate in water, B—0.2% triethylammonium acetate in CH$_3$CN. Corresponding fractions were combined, evaporated, co-evaporated with water (3×10 mL), dissolved in methanol (1 mL) and precipitated with ether (35 mL) to yield 117 as white solid.

MS 298.38 (M+H) H$^1$-NMR (DMSO-d6): 0.75 (s, 3H, 2'-CH$_3$), 3.60-4.00 (m, 4H, sugar), 6.18 (s, 1H, 1'-H), 6.75 (s, 1H, Ar—H$^2$), 7.85 (d, 1H, Ar—H$^7$), 8.25 (d, 1H, Ar—H$^8$).

Example 4

6-hydroxylamino-9-(2'-C-methyl-3',5-diphosphite-β-D-ribofuranosyl)purine (42)

Step 1: Synthesis of 3',5-diphosphite compound 6-hydroxylamino-9-(2'-C-methyl-β-D-ribofuranosyl)purine (30 mg, 0.1 mmol) was dried by co-evaporation with dry DMF (3×1 mL), dissolved in 5 mL of trimethylphosphate and cooled to 0° C. Phosphorous trichloride was added (0.12 mmol) followed by proton sponge (0.1 mmol). The reaction mixture was kept at 0° C. for 2 hours. The reaction was then quenched by (But$_3$N)HCO3, followed by evaporation. The residue was purified by IE HPLC and repurified by RF HPLC as described in Example 26.

$^1$H-NMR: 0.86 (s, 3H, CH$_3$), 4.00-4.28 (m, 3H, sugar), 4.60-4.80 (m, sugar and H$_2$O), 5.56-5.52 (d, 1H, PH), 6.09 (s, 1H, 1'H), 7.68-7.78 (d, 1H, PH), 8.56 & 8.62 (s, 1H, purine); $^{31}$P-NMR: 5.87 (dd, 1P, P-3', $J_{P,H}$=644 Hz, $J_{P,3'H}$=12 Hz), 7.60 (dt, 1P, P-5', $J_{P,H}$=636 Hz, $J_{P,5a'H}$=$J_{P,5b'H}$=6.0 Hz); MS=213 (M/2–H), 427 (M–H)

Step 2: Synthesis of the title compound

The chloropurine nucleotide was co-evaporated with ethanol (3×2 mL), dissolved in 5 mL of ethanol and 0.1 mL of O-trimethylsilylhydroxylamine was added. The mixture was kept at 65° C. for 5 hours, evaporated and purified by RP HPLC in a gradient of acetonitrile in water. Fractions containing the title compound were evaporated.

MS: 211.55 (M/2–H), 424.06 (M–H).

Example 5

7-(2'-C-methyl-β-D-ribofuranosyl)-4-methoxy-lamino-pyrrolo[2,3-d]pyrimidine (118)

Nucleoside 118 was prepared from the nucleoside 141 (example 3, step 1) substituting methoxylamine for hydroxylamine.

Example 6

1-(2'-C-methyl-β-D-ribofuranosyl)-4-hydroxy-lamino-pyrazolo[3,4-d]pyrimidine (120)

Step 1. Synthesis of 2,3,5-tri-O-benzoyl-2'-methyl-1,5-dihydro-pyrazolo[3,4-d]pyrimidin-4-one (142)

Nucleoside 142 was synthesized as described in Example 1 by substitution of 6-bromopurine for 1,5-dihydro-pyrazolo[3,4-d]pyrimidin-4-one.

Step 2. Synthesis of 2,3,5-tri-O-benzoyl-2'-methyl-4-chloro-pyrazolo[3,4-d]pyrimidine (143)

Nucleoside 142 was dissolved in toluene, 10 equivalents of SOCl$_2$ were added and the mixture was heated at 50° C. for 2 hours. The solvents were evaporated in vacuo, the residue was co-evaporated with toluene and purified by flash chromatography on silica gel (toluene-ethyl acetate, 9:1 v/v). Corresponding fractions were evaporated, dissolved in 10 mL of methanol and 5 mL NH$_4$OH was added. Reaction mixture was kept at room temperature overnight and evaporated. The titled nucleoside was isolated by HPLC as described in Example 3, step 2.

Step 3. 1-(2'-C-methyl-β-D-ribofuranosyl)-4-hydroxylamino-pyrazolo[3,4-d]pyrimidine (120)

Nucleoside 143 was transformed to nucleoside 120 as described in Example 3, step 2.

Example 7

1-(2'-C-methyl-β-D-ribofuranosyl)-4-methoxy-lamino-pyrazolo[3,4-d]pyrimidine (119)

Nucleoside 119 was prepared from the nucleoside 143 (Example 6, step 3) substituting hydroxylamine for methoxylamine.

Example 8

7-(2'-C-methyl-β-D-ribofuranosyl)-5-chloro-4-hydroxylamino-pyrrolo[2,3-d]pyrimidine (123)

Nucleoside 117 (0.1 mmol) is dissolved in DMF (0.5 mL) and cooled to 0° C. NCS (0.1 mmol) dissolved in DMF (0.5 mL) is then added dropwise and the reaction stirred for 30 minutes at 0° C. and 30 minutes at room temperature. The reaction is quenched with methanol (5 mL) and then concentrated. Column chromatography (SiO$_2$) with MeOH/DCM affords 123.

Example 9

7-(2'-C-methyl-β-D-ribofuranosyl)-5-bromo-4-hydroxylamino-pyrrolo[2,3-d]pyrimidine (124)

Nucleoside 124 is prepared in the same manner as for 123, substituting NBS for NCS.

Example 10

7-(2'-C-methyl-β-D-ribofuranosyl)-5-methyl-4-hydroxylamino-pyrrolo[2,3-d]pyrimidine (125)

Step 1

Nucleoside 141 (1 mmol) is dissolved in DMF (5 mL) and cooled to 0° C. NBS (1 mmol) dissolved in DMF (5 mL) is then added dropwise and the reaction stirred for 30 minutes at 0° C. and 30 minutes at room temperature. The reaction is quenched with methanol (50 mL) and then concentrated. Column chromatography (SiO$_2$) with MeOH/DCM affords the 7-bromo-6-chloro-7-deazapurine riboside.

Step 2

The nucleoside from Step 1 (0.5 mmol) is dissolved in 10% aqueous dioxane (2.5 mL) and potassium carbonate (1.5 mmol) and palladium tetrakis(triphenyl-phosphine) are added followed by trimethylboroxine (0.5 mmol). The reaction is refluxed for 18 h then filtered through Celite and concentrated. Column chromatography (SiO$_2$) with MeOH/DCM affords the 7-methyl-6-chloro-7-deazapurine riboside.

Step 3

Nucleoside 125 is synthesized as described in Example 3, step 2 using hydroxylamine.

Example 11

7-(2'-C-methyl-β-D-ribofuranosyl)-5-ethyl-4-hydroxylamino-pyrrolo[2,3-d]pyrimidine (128)

Step 1

The nucleoside from Example 10, Step 1 (0.1 mmol) is dissolved in THF (1 mL) and then palladium tetrakis(triphenylphosphine) is added. To this reaction is then added diethyl zinc and the reaction heated to reflux for 6 hours. The reaction is quenched with aqueous NH$_4$Cl and extractively worked up. Column chromatography (SiO$_2$) with MeOH/DCM affords the 7-ethyl-6-chloro-7-deazapurine riboside.

Step 2

Nucleoside 128 is synthesized as described in Example 3, step 2 using hydroxylamine.

Example 12

7-(2'-C-methyl-β-D-ribofuranosyl)-5-cyano-4-hydroxylamino-pyrrolo[2,3-d]pyrimidine (126)

Step 1

The nucleoside from Example 10, step 1 (0.5 mmol) is dissolved in THF (5 mL) and then palladium tetrakis(triphenylphosphine) is added. To this reaction is then added zinc cyanide and the reaction heated to reflux for 6 hours. The reaction is quenched with aqueous $NH_4Cl$ and extractively worked up. Column chromatography ($SiO_2$) with MeOH/DCM affords the 7-cyano-6-chloro-7-deazapurine riboside.

Step 2

Nucleoside 126 is synthesized as described in Example 3, step 2 using hydroxylamine.

Example 13

7-(2'-C-methyl-β-D-ribofuranosyl)-4-hydroxylamino-pyrrolo[2,3-d]pyrimidine 5-carboxylamide (127)

Step 1

The nucleoside from Example 12, step 1 (0.5 mmol) is dissolved in anhydrous ethanol (10 mL) and then saturated with anhydrous HCl. The reaction is stirred at room temperature overnight and then concentrated. The residue is redissolved in ethanol (5 mL) and then water (1 mL) is added and the reaction stirred for 2 hours. The solution is concentrated and purified by column chromatography ($SiO_2$) with MeOH/DCM affording the 7-carboxamide-6-chloro-7-deazapurine riboside.

Step 2

Nucleoside 127 is synthesized as described in Example 3, step 2 using hydroxylamine.

Example 14

7-(2'-C-methyl-β-D-ribofuranosyl)-5-bromo-4-methoxylamino-pyrrolo[2,3-d]pyrimidine (129)

Nucleoside 129 is synthesized from 118 as described in Example 9.

Example 15

7-(2'-C-methyl-β-D-ribofuranosyl)-5-methyl-4-methoxylamino-pyrrolo[2,3-d]pyrimidine (130)

Nucleoside 130 is synthesized as described in Example 3, step 2, substituting methoxylamine for hydroxylamine.

Example 16

7-(2'-C-methyl-β-D-ribofuranosyl)-5-cyano-4-methoxylamino-pyrrolo[2,3-d]pyrimidine (131)

The nucleoside from Example 10, step 2 is converted to 131 as described in Example 15.

Example 17

7-(2'-C-methyl-β-D-ribofuranosyl)-4-methoxylamino-pyrrolo[2,3-d]pyrimidine 5-carboxylamide (132)

The nucleoside from Example 12, step 1 is converted to 132 as described in Example 15.

Example 18

1-(2'-C-methyl-β-D-ribofuranosyl)-3-bromo-4-hydroxylamino-pyrazolo[3,4-d]pyrimidine (133)

Nucleoside 120 is converted to 133 as described in Example 9.

Example 19

1-(2'-C-methyl-β-D-ribofuranosyl)-3-methyl-4-hydroxylamino-pyrazolo[3,4-d]pyrimidine (134)

Nucleoside 134 is synthesized from 143 using conditions described in Example 10.

Example 20

1-(2'-C-methyl-β-D-ribofuranosyl)-3-cyano-4-hydroxylamino-pyrazolo[3,4-d]pyrimidine (135)

Nucleoside 135 is synthesized from 143 using conditions described in Example 12.

Example 21

1-(2'-C-methyl-β-D-ribofuranosyl)-4-hydroxylamino-pyrazolo[3,4-d]pyrimidine-3-carboxamide (136)

Nucleoside 136 is synthesized from 143 using conditions described in Example 13.

Example 22

1-(2'-C-methyl-β-D-ribofuranosyl)-3-bromo-4-methoxylamino-pyrazolo[3,4-d]pyrimidine (137)

Nucleoside 137 is synthesized from compound 119 using conditions described in Example 10.

Example 23

1-(2'-C-methyl-β-D-ribofuranosyl)-3-methyl-4-methoxylamino-pyrazolo[3,4-d]pyrimidine (138)

Nucleoside 138 is synthesized from 143 using conditions described in Example 10, substituting methoxyamine for hydroxyamine.

Example 24

1-(2'-C-methyl-β-D-ribofuranosyl)-3-cyano-4-methoxylamino-pyrazolo[3,4-d]pyrimidine (139)

Nucleoside 139 is synthesized from 143 using conditions described in Example 12, substituting methoxyamine for hydroxyamine.

Example 25

1-(2'-C-methyl-β-D-ribofuranosyl)-4-methoxy-lamino-pyrazolo[3,4-d]pyrimidine-3-carboxamide (140)

Nucleoside 140 is synthesized from 143 using conditions described in Example 13, substituting methoxyamine for hydroxyamine.

Example 26

6-Hydroxylamino-9-β-D-ribofuranosylpurine 5'-Triphosphate

Example 26 is an inactive compound but is included for the purpose of illustrating synthesis of triphosphates of hydroxylamine substituted purines.

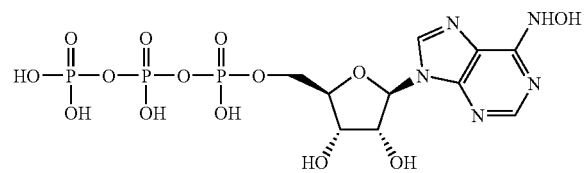

Step 1. Synthesis of 6-chloro-9-β-D-ribofuranosylpurine 5'-triphosphate

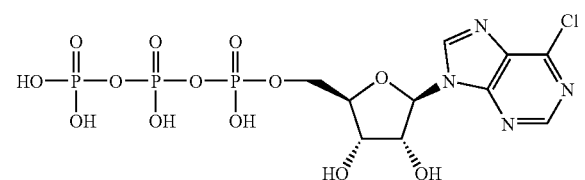

6-chloro-9-β-D-ribofuranosylpurine (27 mg, 0.1 mmol) was co-evaporated 3 times with dry DMF, dissolved in 2 mL of PO(OMe)$_3$, cool to 5° C. and POCl$_3$ (35 μL) and proton sponge (64 mg) were added. The mixture was stirred at 5° C. for 3 h, then tetrabutylammonium pyrophosphate (2 mmol, 4 mL of 0.5M solution in DMF) was added and the mixture was kept for 2 more h at the same temperature. The reaction was quenched with (Et$_3$N)HCO$_3$ buffer (pH 7.5) followed with water. The solvents were evaporated, the residue dissolved in methanol (3 mL) and precipitated with ether (30 mL). The solid residue was purified by IE HPLC on Vidac column (250×10 mm) 0 to 100% B. Buffer A was 25 mM NaH$_2$PO$_4$/Na$_2$HPO$_4$, pH 3, buffer B was 310 mM NaH$_2$PO$_4$/Na$_2$HPO$_4$, pH 3. The last peak was collected, concentrated up to the volume of 5 mL and repurified on RP HPLC on Phenominex column (250×20 mm) in gradient from 0 to 100% of buffer B in buffer A. Buffer A was 0.5 M aqueous solution of triethylammonium acetate, buffer B was 0.5 M acetonitrile solution of triethylammonium acetate. Fractions containing the title compound were combined, evaporated, co-evaporated 3 times with water and lyophilized from water.

MS 524.94 (M–H), P$^{31}$-NMR (DMSO-d6): –10.31 and –11.41 (d, 1P, P-α & P-γ), –22.66 (t, 1P, P-β).

Step 2. Synthesis of 6-hydroxylamino-9-(2'-C-methyl-β-D-ribofuranosyl)purine 5'-triphosphate Triphosphate from the Step 1 was co-evaporated 3 times with dry ethanol, dissolved in dry ethanol and O-trimethylsilyl hydroxylamine (10 mmol) was added. The mixture was heated for 0.5 h at 65° C., neutralized with HCl/dioxane and evaporated. The crude mixture was separated by RP HPLC on a Phenominex column (250×20 mm) using gradient of acetonitrile in water from 0 to 100%. Corresponding fractions were concentrated and lyophilized from water.

MS 260.52 (1/2M–H), P$^{31}$-NMR (DMSO-d6): –10.70 and –11.41 (d, 1P, P-α & P-γ), –23.03 (t, 1P, P-γ).

Example 27

6-Hydroxylamino-9(2'-methyl-β-D-ribofuranosylpurine 5'-Triphosphate (227)

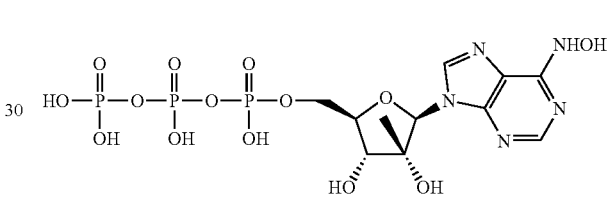

The title compound was synthesized from 6-chloro-9-(2'-C-methyl-β-D-ribofuranosyl)purine as described in Example 26, Step 1-2.

MS 267.52 (1/2M–H), 535.99 (M–H). P$^{31}$-NMR (DMSO-d6): –10.70 (2P, P-α & P-γ), –23.00 (1P, P-β).

Example 28

1-(2'-C-methyl-β-D-ribofuranosyl)-4-hydroxy-lamino-1H-pyrazolo[3,4-d]pyrimidine (120)

Step 1. Synthesis of 4-chloro-1H-pyrazolo[3,4-d]pyrimidine

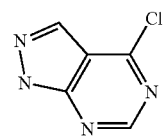

4-Chloro-1H-pyrazolo[3,4-d]pyrimidine was synthesized from 4-hydroxypyrazolo[3,4-d]pyrimidine and POCl$_3$ as described by R. Robins in J. Am. Chem. Soc., 1957, V. 79, N20, P. 6407-6415.

Step 2. Synthesis of 1-[2'-C-methyl-3',5'-bis-O-(2,4-dichlorophenylmethyl)-β-D-ribofuranosyl]-4-chloro-1H-pyrazolo[3,4-d]pyrimidine

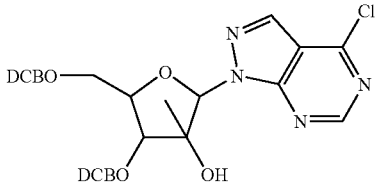

The title compound was synthesized as described in Example 1, Step 1 from 4-chloro-1H-pyrazolo[3,4-d]pyrimidine (Step 1) and 1-O-methyl-3,5-bis-O-(2,4-dichlorophenylmethyl)-2'-C-methyl-β-D-ribofuranoside

MS: 525.07 (M+NH$_4^+$).

Step 3. Synthesis of 1-(2'-C-methyl-β-D-ribofuranosyl)-4-chloro-1H-pyrazolo[3,4-d]pyrimidine

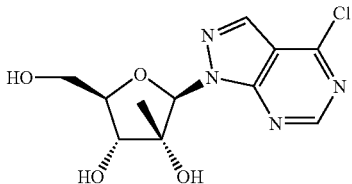

The title compound was synthesized from the nucleoside from Step 2 as described in Example 1, Step 2.

MS: 301.93 (M+H

Step 4. Synthesis of 1-(2'-C-methyl-β-D-ribofuranosyl)-4-hydroxylamino-1H-pyrazolo[3,4-d]pyrimidine

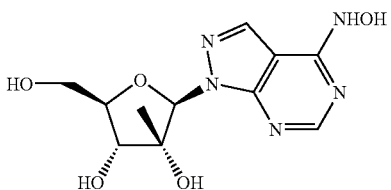

The title compound was synthesized from the nucleoside from Step 3 as described in Example 1, Step 3. MS: 298.13 (M+H).

Example 29

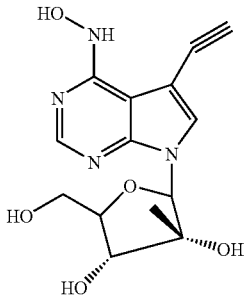

2-(4-Amino-5-ethynyl-pyrrolo[2,3-d]pyrimidin-7-yl)-5-hydroxymethyl-3-methyl-tetrahydro-furan-3,4-diol (229)

Step 1. Synthesis of 4-Chloro-5-iodo-7H-pyrrolo[2,3-d]pyrimidine

4-Chloro-5-iodo-7H-pyrrolo[2,3-d]pyrimidine was synthesized from 6-chloropurine (Toronto Research) as described in A. Gangjee et. al., J. Med. Chem. (2003) 46, 591-600.

Step 2. Synthesis of 4-Chloro-5-trimethylsilanylethynyl-7H-pyrrolo[2,3-d]pyrimidine 4-Chloro-5-trimethylsilanylethynyl-7H-pyrrolo[2,3-d]pyrimidine was synthesized from 4-chloro-5-iodo-7H-pyrrolo[2,3-d]pyrimidine (Step 1) as described in A. Gangjee et. al., J. Med. Chem. (2003) 46, 591-600.

Step 3. Synthesis of 2-(4-Chloro-5-trimethylsilanylethynyl-pyrrolo[2,3-d]pyrimidin-7-yl)-4-(2,4-dichloro-benzyloxy)-5-(2,4-dichloro-benzyloxymethyl)-3-methyl-tetrahydro-furan-3-ol 2-(4-Chloro-5-trimethylsilanylethynyl-pyrrolo[2,3-d]pyrimidin-7-yl)-4-(2,4-dichloro-benzyloxy)-5-(2,4-dichloro-benzyloxymethyl)-3-methyl-tetrahydrofuran-3-ol (0.440 g, 2.08 mmol) from step 2 was suspended in 31 mL of dry acetonitrile. 0.063 g (2.08 mmol) of NaH (60% in oil) was added and the mixture was stirred for 4 h at ambient temperature under an argon atmosphere. Meanwhile, 1-O-Methyl-3,5-bis-O-(2,4-dichlorophenylmethyl)-2'-C-methyl-β-D-ribofuranoside (0.339 g, 0.902 mmol) was dissolved in 10 mL of dry dichloromethane, cooled to 0° C. and HBr (0.75 mL, 30% w/w in AcOH) was added drop wise. The reaction was maintained for 1 h at 0° C. and for an additional 2.5 h at ambient temperature and then the solvent was evaporated. The mixture was 3 times co-evaporated with dry toluene, dissolved in 10 mL of dry acetonitrile and added to the sodium salt of the base. The reaction mixture was kept at room temperature overnight and evaporated to dryness. The residue was distributed between ethyl acetate and water. The water fraction was extracted with ethyl acetate (4×100 mL). The combined organic fractions were washed with brine, dried over sodium sulfate then evaporated. The residue was purified by flash chromatography on silica gel (ethyl acetate/dichloromethane 5:100 v/v) to yield 0.215 g (33%) of protected nucleoside. MS: 714.08 (M+1).

Step 4. 2-(4-Chloro-5-trimethylsilanylethynyl-pyrrolo[2,3-d]pyrimidin-7-yl)-5-hydroxymethyl-3-methyl-tetrahydro-furan-3,4-diol To the solution of the product from Step 3 (0.215 g, 0.3 mmol) in dichloromethane (8 mL) maintained at −78° C. was added boron trichloride (1M in dichloromethane) (2.9 mL, 3.0 mmol). The mixture was stirred at −78° C. for 1 h, then at −20° C. overnight. The reaction was quenched with dichloromethane/methanol 1:1 (7.5 mL), stirred at −20° C. for 0.5 h and neutralized at 0° C. with aqueous ammonia. The solid was filtered, washed with dichloromethane/methanol 1:1 and the combined extracts evaporated in vacuo. The residue was purified on silica gel column with chloroform/methanol (10:1 v/v) as eluent. Corresponding fractions were combined, concentrated to yield 0.082 g (70%) of the deprotected nucleoside.

Step 5. 2-(5-Ethynyl-4-hydroxyamino-pyrrolo[2,3-d]pyrimidin-7-yl)-5-hydroxymethyl-3-methyl-tetrahydro-furan-3,4-diol The compound from Step 4 is suspended in dry ethanol and O-trimethylsilyl hydroxylamine (10 eq.) is added. The mixture is refluxed for 2 hours, evaporated and the crude mixture is purified by RP HPLC on a Phenominex column (250×20 mm) using gradient of acetonitrile in water from 0 to 30% over 30 minutes at 10 mL/minute.

Example 30

2-(4-Hydroxyamino-5-vinyl-pyrrolo[2,3-d]pyrimidin-7-yl)-5-hydroxymethyl-3-methyl-tetrahydrofuran-3,4-diol (230)

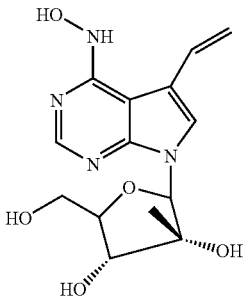

The title compound from Example 29 is dissolved in THF and placed under hydrogen (1 atm) in the presence of Lindlar's catalyst until one mole of hydrogen is consumed.

Example 31

2-(4-Hydroxyamino-5-oxazol-5-yl-pyrrolo[2,3-d]pyrimidin-7-yl)-5-hydroxymethyl-3-methyl-tetrahydro-furan-3,4-diol (231)

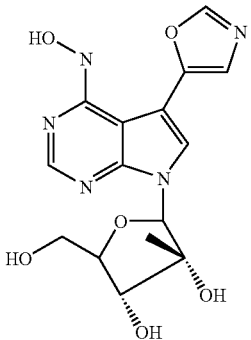

Step 1. Synthesis of 4-Chloro-7-(3,4-dihydroxy-5-hydroxymethyl-3-methyl-tetrahydro-furan-2-yl)-7H-pyrrolo[2,3-d]pyrimidine-5-carbaldehyde 4-Chloro-7-(3,4-dihydroxy-5-hydroxymethyl-3-methyl-tetrahydrofuran-2-yl)-7H-pyrrolo[2,3-d]pyrimidine-5-carbaldehyde is synthesized through a multi-step reaction pathway according to the procedure described in S. Watanabe and T. Ueda. Nucleosides and Nucleotides (1983) 2(2), 113-125. However 2-(4-chloro-pyrrolo[2,3-d]pyrimidin-7-yl)-5-hydroxymethyl-3-methyl-tetrahydrofuran-3,4-diol is used in place of tubercidin.

Step 2. 2-(4-Chloro-5-oxazol-5-yl-pyrrolo[2,3-d]pyrimidin-7-yl)-5-hydroxymethyl-3-methyl-tetrahydro-furan-3,4-diol To the compound from Step 1 is added tosylmethyl isocyanide (1 eq.) in MeoH containing $K_2CO_3$ (1 eq.) and the mixture is heated to reflux until starting material is consumed. The solvent is removed in vacuo and the crude mixture purified by RP HPLC on a Phenominex column (250×20 mm) using a gradient of acetonitrile in water from 0 to 30% over 30 minutes at 10 mL/minute.

Step 3. 2-(4-Hydroxyamino-5-oxazol-5-yl-pyrrolo[2,3-d]pyrimidin-7-yl)-5-hydroxymethyl-3-methyl-tetrahydro-furan-3,4-diol The compound from Step 2 is suspended in dry ethanol and O-trimethylsilyl hydroxylamine (10 eq.) is added. The mixture is refluxed for 2 h, evaporated and the crude mixture purified by RP HPLC on a Phenominex column (250×20 mm) using a gradient of acetonitrile in water from 0 to 30% over 30 minutes at 10 mL/minute to yield the title compound.

Example 32

Preparation of the intermediate methyl 2-methyl-3,5-bis(DCB)-ribose

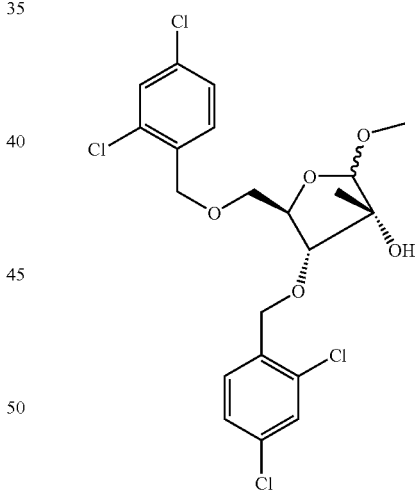

Step 1: Preparation of methyl-2,3,5-tris-O-(2,4-dichlorobenzyl)-1-O-methyl-D-ribofuranose The title compound is synthesized using the methods described in Martin, P.; Helv. Chim. Acta, 1995, 78, 486 starting with commercially available D-ribose.

Step 2: Preparation of methyl-3,5-bis-O-(2,4-dichlorobenzyl)-1-O-methyl-D-ribofuranose To a solution of the product of Step 1 (171.60 g, 0.2676 mol) in 1.8 L $CH_2Cl_2$ that was cooled to 0° C., was added dropwise a solution of stannous chloride (31.522 mL, 0.2676 mol) in 134 mL $CH_2Cl_2$ while stirring. After the solution was kept at 3° C. for 27 hours, another 5.031 ml of $SnCl_4$ (0.04282 mol) was added and the solution was kept at 3° C. overnight. After 43 hours the reaction was quenched by carefully adding the solution to 1.9 L saturated $NaHCO_3$ solution. Tin salts were removed via filtration through celite after which the organic phace was isolated, dried with $MgSO_4$ and evaporated in vacuo. The yield of raw, dark yellow oil was 173.6 g, which contains 2,4-dibenzoyl chloride. The crude oil was used directly in the next step without further purification.

Step 3: Preparation of methyl-2-O-acetyl-3,5-bis-O-(2,4-dichlorobenzyl)-1-O-methyl-D-ribofuranose To the solution of raw oil from Step 2 above (173.6 g, 0.3600 mol) in 1.379 L pyridine, were added $Ac_2O$ (33.970 mL, 0.3600 mol) and DMAP (1.3766 g, 0.01127 mol). After 21 hours of stirring at room temperature 1.4 L $H_2O$ were added. The solution was acidified with 1.45 L concentrated HCL. The acidified product was extracted with EtOAc, dried with $MgSO_4$ and concentrated in vacuo. The residue was isolated as 85.75 g (0.1636 mol) of clear oil.

Step 4: Preparation of 3,5-bis-O-(2,4-dichlorobenzyl)-1-O-methyl-D-ribofuranose

The compound prepared in Step 3 above (85.75 g, 0.1636 mol) in 820 mL of saturated methanolic potassium carbonate was stirred at ambient temperature for 45 minutes and then concentrated in vacuo. The oily residue was suspended in 820 mL of $CH_2Cl_2$, washed with water (493 mL+5×328 mL) and brine (328 mL), dried ($NaSO_4$), filtered, and concentrated to give the product. The oil (75.93 g, 0.1573 mol) was immediately used in the next step without further purification.

Step 5: Preparation of 3,5-bis-O-(2,4-dichlorobenzyl)-1-O-methyl-D-erythro-pentafuranos-2-ulose To an ice-cold suspension of Dess-Martin periodinane (106.75 g, 0.2517 mol) in 740 mL anhydrous $CH_2Cl_2$, under argon, was added a solution of the product of Step 4 above in 662 mL anhydrous $CH_2Cl_2$ dropwise over 0.5 hours. The reaction mixture was stirred at 0° C. for 0.5 hours and then at room temperature for 6 days. The mixture was diluted with 1.26 L anhydrous $Et_2O$ and poured into an ice-cold mixture of $Na_2S_2O_3 5H_2O$ (241.2 g, 1.5258 mol) in 4.7 L saturated aqueous $NaHCO_3$. The layers were separated, and the organic layer was washed with 1.3 L saturated aqueous $NaHCO_3$, 1.7 L water and 1.3 L brine, dried with $MgSO_4$, filtered and evaporated to give the target compound. This compound (72.38 g, 0.1507 mol) was used without further purification in the next step.

Step 6: Preparation of the title compound

A solution of MeMgBr in 500 mL anhydrous $Et_2O$ at 55° C. was added dropwise to a solution of the product of Step 5 above (72.38 g, 0.1507 mol), also in 502 mL anhydrous $Et_2O$. The reaction mixture was allowed to warm to −30° C. and stirred mechanically for 4 hours at −30° C. to −15° C., then poured into 2 L ice cold water. After stirring vigorously at ambient temperature for 0.5 hours, the mixture was filtered through a Cleite pad (14×5 cm), which was thoroughly washed with $Et_2O$. The organic layer was dried with $MgSO_4$, filtered and concentrated in vacuo. The residue was dissolved in hexanes (~1 mL per gram crude), applied to a silica gel column (1.5 L silica gel in hexanes) and eluted with hexanes and [4:1 hexanes:ethyl acetate, v/v] to give 53.58 g (0.1080 mol) of the final purified product. The morphology of the title compound was that of an off-yellow, viscous oil.

MS: m/z 514.06 ($M+NH_4^+$).

BIOLOGICAL EXAMPLES

Example 1

Anti-Hepatitis C Activity

Compounds of this invention exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274: 10807-10815, 1999; and Yamashita et al., *Jnl. of Bio. Chem.*, 273:15479-15486, 1998.

WO 97/12033, filed on Sep. 27, 1996, by Emory University, listing C. Hagedorn and A. Reinoldus as inventors, which claims priority to U.S. Ser. No. 60/004,383, filed on September 1995, describes an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1(Supp 4) 18-24.

Screens that measure reductions in kinase activity from HCV drugs are disclosed in U.S. Pat. No. 6,030,785, to Katze et al., U.S. Patent No. Delvecchio et al., and U.S. Pat. No. 5,759,795 to Jubin et al. Screens that measure the protease inhibiting activity of candidate HCV drugs are disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) is used for screening of compounds of the present invention for HCV RNA dependent RNA polymerase. The ET cell line is stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells are grown in DMEM, supplemented with 10% fetal calf serum, 2 mM Glutamine, Penicillin (100 IU/mL)/Streptomycin (100 µg/ml), 1× nonessential amino acids, and 250 µg/mL G418 ("Geneticin"). They are all available through Life Technologies (Bethesda, Md.). The cells are plated at 0.5-1.0×$10^4$ cells/well in the 96 well plates and incubated for 24 h before adding nucleoside analogs. Then the compounds each at 5 and 50 µM will be added to the cells. Luciferase activity will be measured 48-72 hours later by adding a lysis buffer and the substrate (Catalog number Glolysis buffer E2661 and Bright-Glo leuciferase system E2620 Promega, Madison, Wis.). Cells should not be too confluent during the assay. Percent inhibition of replication will be plotted relative to no compound control. Under the same condition, cytotoxicity of the compounds will be determined using cell proliferation reagent, WST-1 (Roche, Germany). The compounds showing antiviral activities, but no significant cytotoxicities will be chosen to determine $IC_{50}$ and $TC_{50}$.

Example 3

Cloning and Expression of Recombinant HCV-NS5b

The coding sequence of NS5b protein is cloned by PCR from pFKI$_{389}$luc/NS3-3'/ET as described by Lohmann, V., et al. (1999) *Science* 285, 110-113 using the following primers:
aggacatggatccgcggggtcgggcacgagacag (SEQ. ID. NO. 1)
aaggctggcatgcactcaatgtcctacacatggac (SEQ. ID. NO. 2)
The cloned fragment is missing the C terminus 21 amino acid residues. The cloned fragment is inserted into an IPTG-inducible expression plasmid that provides an epitope tag (His)6 at the carboxy terminus of the protein.

The recombinant enzyme is expressed in XL-1 cells and after induction of expression, the protein is purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a poly-A template (1000-10000 nucleotides) and oligo-$U_{12}$ primer. Alternatively, a portion of the HCV genome is used as template and radiolabeled GTP is used. Typically, the assay mixture (50 µL) contains 10 mM Tris-HCl (pH7.5), 5 mM $MgCl_2$, 0.2 mM EDTA, 10 mM KCl, 1 unit/µL RNA sin, 1 mM DTT, 10 µM each of NTP, alpha-[$^{32}$P]-GTP, 10 ng/µL polyA template and 1 ng/µL oligou primer. Test compounds are dissolved in water containing 0 to 1% DMSO. Typically, compounds are tested at concentrations between 1 nM and 100 µM. Reactions are started with addition of enzyme and allowed to continue at room temperature or 30° C. for 1 to 2 h. Reactions are quenched with 20 µL 10 mM EDTA and reaction mixtures (50 µL) spotted on DE81 filter disc to capture the radiolabelled RNA products. After washing with 0.5 mM $Na_2HPO_4$ (3 times), water (1 time) and ethanol (1 time) to remove unincorporated NTP, the discs are dried and the incorporation of radioactivity is determined by scintillation counting.

FORMULATION EXAMPLES

The following are representative pharmaceutical formulations containing a compound of Formula IV or IVA.

Example 1

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
| --- | --- |
| compound of this invention | 0.2 mg-20 mg |
| sodium acetate buffer solution, 0.4 M | 2.0 ml |
| HCl (1N) or NaOH (1N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| compound of the invention | 500 mg |
| Witepsol ® H-15 | balance |

From the foregoing description, various modifications and changes in the above described invention will occur to those skilled in the art. All such modifications coming within the scope of the appended claims are intended to be included therein.

substituted alkenyl,
alkynyl,
substituted alkynyl;

$R^{13}$ is selected from the group consisting of hydrogen, alkyl, and substituted alkyl;

$R^{14}$ is selected from the group consisting of hydrogen, alkyl, and substituted alkyl;

B is selected from the group consisting of >CH, >C—CN, >C—$NO_2$, >C-alkyl, >C-substituted alkyl, >C-alkenyl, >C-substituted alkenyl, >C-alkynyl, >C-substituted alkynyl, >C—$NHCONH_2$, >C—$CONR^{15}R^{16}$, >C—$COOR^{15}$, >C-hydroxy, >C-alkoxy, >C-amino, >C-alkylamino, >C-dialkylamino, >C-halogen, >C-(1,3-oxazol-2-yl), >C-(1,3-oxazol-5-yl), >C-(1,3-thiazol-

What is claimed is:

1. A compound of Formula:

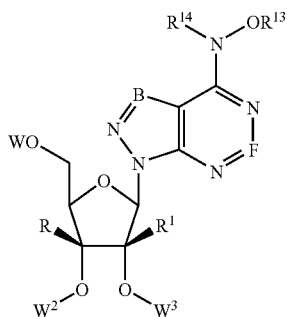

wherein R and $R^1$ are independently selected from the group consisting of:
hydrogen,
alkyl,
substituted alkyl,
alkenyl, 2-yl), >C-(imidazol-2-yl), >C-(2-oxo-[1,3]dithiol-4-yl), >C-(furan-2-yl), and >C-(2H-[1,2,3]triazol-4-yl);

F is selected from >C—CN, >C—$NO_2$, >C-alkyl, >C-substituted alkyl, >C-alkenyl, >C-substituted alkenyl, >C-alkynyl, >C-substituted alkynyl, >C—$NHCONH_2$, >C—$CONR^{15}R^{16}$, >C—$COOR^{15}$, >C-alkoxy, >C-(1,3-oxazol-2-yl), >C-(1,3-oxazol-5-yl), >C-(1,3-thiazol-2-yl), >C-(imidazol-2-yl), >C-(2-oxo-[1,3]dithiol-4-yl), >C-(furan-2-yl), >C-(2H-[1,2,3]triazol-4-yl), and >C—Y, where Y is selected from the group consisting of hydrogen, halo, hydroxy, alkylthioether, and —$NR^3R^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;

$R^{15}$ and $R^{16}$ are independently selected from the group consisting of:

hydrogen,
alkyl,
substituted alkyl,
cycloalkyl,
substituted cycloalkyl,
aryl,
substituted aryl,
heteroaryl,
substituted heteroaryl, and
$R^{15}$ and $R^{16}$ together with the nitrogen atom to which they are attached may form a heterocycloalkyl, substituted heterocycloalkyl, heteroaryl, or substituted heteroaryl;
W, $W^2$, and $W^3$ are independently selected from the group consisting of:
hydrogen,
a phosphate,
a phosphonate,
a monofluorophosphate,
acyl, and
a sulfonate ester,
and pharmaceutically acceptable prodrugs and salts thereof;
wherein
substituted alkyl refers to an alkyl group having from 1 to 3 selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
alkoxy refers to alkyl-O—;
substituted alkoxy refers to (substituted alkyl)-O—:
acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—cycloalkyl-C(O)—, substituted cycloalkyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—;
acylamino refers to —C(O)NRR, where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R is joined to form together with the nitrogen atom a heterocyclyl or substituted heterocyclyl ring;
acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl- C(O)O—, aryl-C(O)O—, substituted aryl-C(O)O—, cycloalkyl-C(O)O—, substituted cycloalkyl- C(O)O—, heteroaryl-C(O)O—, substituted heteroaryl-C(O)O—, heterocyclyl-C(O)O—, and substituted heterocyclyl-C(O)O—:
substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to unsaturated carbon atom;
substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
amino refers to —$NH_2$;
substituted amino refers to —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, or where R' and R" are joined, together with the nitrogen bound thereto to form a heterocyclyl or substituted heterocyclyl group provided that R' and R" are both not hydrogen;
aminoacyl refers to a moiety selected from the group consisting of —NRC(O)alkyl, —NRC(O)substituted alkyl, —NRC(O)cycloalkyl, —NRC(O)substituted cycloalkyl, —NRC(O) alkenyl, —NRC(O)substituted alkenyl, —NRC(O)alkynyl, —NRC(O)substituted alkynyl, —NRC(O)aryl, —NRC(O) substituted aryl, —NRC(O)heteroaryl, —NRC(O)substituted heteroaryl, —NRC(O)heterocyclyl, and —NRC(O) substituted heterocyclyl where R is hydrogen or alkyl;
aryl refers to a monovalent aromatic carbocyclic group of from 6 to 14 carbon atoms having a single ring or multiple condensed rings, which condensed rings may or may not be aromatic;
substituted aryl refers to an aryl group that is substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;
aryloxy refers to aryl-O—;
substituted aryloxy refers to (substituted aryl)-O—;
carboxyl refers to —COOH or a salt thereof;
carboxyl ester refers to a moiety selected from the group consisting of —C(O)O-alkyl, —C(O)O-substituted alkyl, —C(O)Oaryl, and —C(O)O-substituted aryl;
cycloalkyl refers to a cyclic alkyl group of from 3 to 10 carbon atoms having single or multiple cyclic rings;
substituted cycloalkyl refers to a cycloalkyl group having from 1 to 5 substituents selected from the group consisting of oxo (═O), thioxo (═S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
cycloalkoxy refers to a —O-cycloalkyl group;
substituted cycloalkoxy refers to a —O-(substituted cycloalkyl) group;
halogen refers to fluoro, chloro, bromo and iodo;
heteroaryl refers to an aromatic group of from 1 to 10 carbon atoms and 1 to 4 heteroatoms selected from the group consisting of oxygen, nitrogen and sulfur within a single ring or multiple condensed rings;

substituted heteroaryl refers to a heteroaryl group substituted with from 1 to 3 substituents selected the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O—(substituted heteroaryl);

heterocyclyl or heterocyclic refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more of the rings can be cycloalkyl, aryl or heteroaryl provided that the point of attachment is through the heterocyclyl ring;

substituted heterocyclyl or heterocyclic refers to a heterocycle group substituted with from 1 to 3 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl;

substituted heterocyclyloxy refers to —O-(substituted heterocyclyl);

phosphate refers to a moiety selected from the group consisting of —OP(O)(OH)$_2$ (monophosphate),—OP(O)(OH)OP(O)(OH)$_2$ (diphosphate) and —OP(O)(OH)OP(O)(OH)OP(O)(OH)$_2$ (triphosphate) or salts thereof including partial salts thereof;

phosphonate refers to a moiety selected from the group consisting of —OP(O)(R)(OH), —OP(O)(OR), and salts thereof including partial salts thereof, wherein each R is independently selected from hydrogen, alkyl, substituted alkyl, carboxylic acid, and carboxyl ester;

sulfonate ester refers to —SO$_2$OR where R is selected from the group consisting of alkyl, substituted alkyl, alkenyl, substituted alkenyl, aryl, substituted aryl, heteroaryl, substituted heteroaryl, heterocyclyl and substituted heterocyclyl;

thiol refers to —SH;

thioalkyl or alkylthioether refers to —S-alkyl;

substituted thioalkyl refers to —S-(substituted alkyl);

thiocycloalkyl refers to —S-cycloalkyl;

substituted thiocycloalkyl refers to —S-(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclyl refers to —S-heterocyclyl; and substituted thioheterocyclyl refers to —S-(substituted heterocyclyl).

2. The compound according to claim 1, wherein R and $R^1$ are not both hydrogen.

3. The compound according to claim 1, wherein B is >C-Q, F is >CH or >C—Y and where Q is selected from the group consisting of hydrogen, halo, cyano, acylamido, alkyl, alkenyl and alkynyl.

4. The compound according to claim 3, wherein Q is selected from the group consisting of hydrogen, chloro, bromo, cyano, H$_2$NC(O)—, methyl, ethyl, vinyl and acetylenyl.

5. A compound of Formula:

wherein R and $R^1$ are independently selected from the group consisting of:
hydrogen,
alkyl,
substituted alkyl,
alkenyl,
substituted alkenyl,
alkynyl,
substituted alkynyl;

provided that R and $R^1$ are not both hydrogen;

$R^{13}$ is selected from the group consisting of hydrogen, alkyl, and substituted alkyl;

$R^{14}$ is selected from the group consisting of hydrogen, alkyl, and substituted alkyl;

B is selected from the group consisting of >CH, >C—CN, >C—NO$_2$, >C-alkyl, >C-substituted alkyl, >C—NHCONH$_2$, >C—CONR$^{15}$R$^{16}$, >C—COOR$^{15}$, >C-hydroxy, >C-alkoxy, >C-amino, >C-alkylamino, >C-dialkylamino, >C-halogen, >C-(1,3-oxazol-2-yl), >C-(1,3-thiazol-2-yl) and >C-(imidazol-2-yl);

F is selected from >CH, >C—CN, >C—NO$_2$, >C-alkyl, >C-substituted alkyl, >C—NHCONH$_2$, >C—CONR$^{15}$R$^{16}$, >C—COOR$^{15}$, >C-alkoxy, >C-(1,3-oxazol-2-yl), >C-(1,3-thiazol-2-yl), >C-(imidazol-2-yl), and >C—Y, where Y is selected from the group consisting of hydrogen, halo, hydroxy, alkylthioether, and —NR$^3$R$^4$ where $R^3$ and $R^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where $R^3$ and $R^4$ are joined to form, together with the nitrogen atom bond thereto, a heterocyclic group, provided that only one of $R^3$ and $R^4$ is hydroxy, alkoxy, or substituted alkoxy;

$R^{15}$ and $R^{16}$ are independently selected from the group consisting of:
hydrogen,
alkyl,
substituted alkyl, cycloalkyl,
substituted cycloalkyl,
aryl,
substituted aryl,
heteroaryl,
substituted heteroaryl, and
$R^{15}$ and $R^{16}$ together with the nitrogen atom to which they are attached may form a heterocycloalkyl, substituted heterocycloalkyl, heteroaryl, or substituted heteroaryl;
W is selected from the group consisting of:
hydrogen,
a phosphate,
a phosphonate,
acyl,
alkyl, and
a sulfonate ester,
and pharmaceutically acceptable salts thereof;
wherein
substituted alkyl refers to an alkyl group having from 1 to 3 selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
alkoxy refers to alkyl-O—;
substituted alkoxy refers to (substituted alkyl)-O—;
acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl—C(O)—, substituted cycloalkyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—;
acylamino refers to —C(O)NRR, where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R is joined to form together with the nitrogen atom a heterocyclyl or substituted heterocyclyl ring;
acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—:
substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to unsaturated carbon atom;
substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
amino refers to —NH$_2$;
substituted amino refers to —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, or where R' and R" are joined, together with the nitrogen bound thereto to form a heterocyclyl or substituted heterocyclyl group provided that R' and R" are both not hydrogen;
aminoacyl refers to a moiety selected from the group consisting of —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclyl, and —NRC(O)substituted heterocyclyl where R is hydrogen or alkyl;
aryl refers to a monovalent aromatic carbocyclic group of from 6 to 14 carbon atoms having a single ring or multiple condensed rings, which condensed rings may or may not be aromatic;
substituted aryl refers to an aryl group that is substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;
aryloxy refers to aryl-O—;
substituted aryloxy refers to (substituted aryl)-O—;
carboxyl refers to —COOH or a salt thereof;
carboxyl ester refers to a moiety selected from the group consisting of —C(O)O-alkyl, —C(O)O-substituted alkyl, —C(O)Oaryl, and —C(O)O-substituted aryl; cycloalkyl refers to a cyclic alkyl group of from 3 to 10 carbon atoms having single or multiple cyclic rings;
substituted cycloalkyl refers to a cycloalkyl group having from 1 to 5 substituents selected from the group consisting of oxo (═O), thioxo (═S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
cycloalkoxy refers to a —O-cycloalkyl group;
substituted cycloalkoxy refers to a —O-(substituted cycloalkyl) group;
halogen refers to fluoro, chloro, bromo and iodo;
heteroaryl refers to an aromatic group of from 1 to 10 carbon atoms and 1 to 4 heteroatoms selected from the group consisting of oxygen, nitrogen and sulfur within a single ring or multiple condensed rings;
substituted heteroaryl refers to a heteroaryl group substituted with from 1 to 3 substituents selected the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O—heteroaryl;

substituted heteroaryloxy refers to —O—(substituted heteroaryl);

heterocyclyl or heterocyclic refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more of the rings can be cycloalkyl, aryl or heteroaryl provided that the point of attachment is through the heterocyclyl ring;

substituted heterocyclyl or heterocyclic refers to a heterocycle group substituted with from 1 to 3 substituents selected from the group consisting of oxo (=O), thioxo (=S). alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl;

substituted heterocyclyloxy refers to —O-(substituted heterocyclyl);

phosphate refers to a moiety selected from the group consisting of —OP(O)(OH)$_2$ (monophosphate),—OP(O)(OH)OP(O)(OH)$_2$ (diphosphate) and —OP(O)(OH)OP(O)(OH)OP(O)(OH)$_2$ (triphosphate) or salts thereof including partial salts thereof;

phosphonate refers to a moiety selected from the group consisting of —OP(O)(R)(OH), —OP(O)(OR), and salts thereof including partial salts thereof, wherein each R is independently selected from hydrogen, alkyl, substituted alkyl, carboxylic acid, and carboxyl ester;

sulfonate ester refers to —SO$_2$OR where R is selected from the group consisting of alkyl, substituted alkyl, alkenyl, substituted alkenyl, aryl, substituted aryl, heteroaryl, substituted heteroaryl, heterocyclyl and substituted heterocyclyl;

thiol refers to —SH;

thioalkyl or alkylthioether refers to —S-alkyl;

substituted thioalkyl refers to —S-(substituted alkyl);

thiocycloalkyl refers to —S-cycloalkyl;

substituted thiocycloalkyl refers to —S-(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclyl refers to —S-heterocyclyl; and substituted thioheterocyclyl refers to —S-(substituted heterocyclyl).

6. A compound of Formula IE:

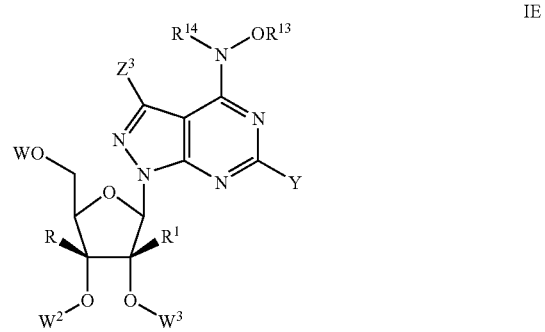

wherein R and $R^1$ are independently selected from the group consisting of:
hydrogen,
alkyl,
substituted alkyl,
alkenyl,
substituted alkenyl,
alkynyl, and
substituted alkynyl;

$R^{13}$ is selected from the group consisting of hydrogen, alkyl, and substituted alkyl;

$R^{14}$ is selected from the group consisting of hydrogen, alkyl, and substituted alkyl;

Y is selected from the group consisting of:
hydrogen,
halo,
hydroxy,
alkylthioether, and
—NR$^3$R$^4$ where R$^3$ and R$^4$ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where R$^3$ and R$^4$ are joined to form, together with the nitrogen atom bond thereto, a heterocyclic group, provided that only one of R$^3$ and R$^4$ is hydroxy, alkoxy, or substituted alkoxy;

$Z^3$ is selected from the group consisting of:
hydrogen,
halo,
hydroxy,
alkyl,
substituted alkyl,
alkenyl,
substituted alkenyl,
alkynyl,
substituted alkynyl,
cyano
carboxyl,
carboxyl ester,
acylamino,
1,3-oxazol-2-yl,
1,3-oxazol-5-yl,
1,3-thiazol-2-yl,
imidazol-2-yl,
2-oxo-[1,3]dithiol-4-yl,
furan-2-yl,
2H-[1,2,3]triazol-4-yl, and —NR³R⁴ where R³ and R⁴ are independently selected from the group consisting of hydrogen, hydroxy, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclic, substituted heterocyclic and where R³ and R⁴ are joined to form, together with the nitrogen atom bond thereto, a heterocyclic group, provided that only one of R³ and R⁴ is hydroxy, alkoxy, or substituted alkoxy;

W, W², and W³ are independently selected from the group consisting of:
hydrogen,
a phosphate,
a phosphonate,
a monofluorophosphate,
acyl, and
a sulfonate ester,
and pharmaceutically acceptable prodrugs and salts thereof;

wherein
substituted alkyl refers to an alkyl group having from 1 to 3 selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

alkoxy refers to alkyl-O—;

substituted alkoxy refers to (substituted alkyl)-O—:

acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—;

acylamino refers to —C(O)NRR, where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R is joined to form together with the nitrogen atom a heterocyclyl or substituted heterocyclyl ring;

acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—:

substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to unsaturated carbon atom;

substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

amino refers to —NH₂;

substituted amino refers to —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, or where R' and R" are joined, together with the nitrogen bound thereto to form a heterocyclyl or substituted heterocyclyl group provided that R' and R" are both not hydrogen;

aminoacyl refers to a moiety selected from the group consisting of —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclyl, and —NRC(O)substituted heterocyclyl where R is hydrogen or alkyl;

aryl refers to a monovalent aromatic carbocyclic group of from 6 to 14 carbon atoms having a single ring or multiple condensed rings, which condensed rings may or may not be aromatic;

substituted aryl refers to an aryl group that is substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —COOH or a salt thereof;

carboxyl ester refers to a moiety selected from the group consisting of —C(O)O-alkyl, —C(O)O-substituted alkyl, —C(O)Oaryl, and —C(O)O-substituted aryl; cycloalkyl refers to a cyclic alkyl group of from 3 to 10 carbon atoms having single or multiple cyclic rings;

substituted cycloalkyl refers to a cycloalkyl group having from 1 to 5 substituents selected from the group consisting of oxo (═O), thioxo (═S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

cycloalkoxy refers to a —O-cycloalkyl group;

substituted cycloalkoxy refers to a —O-(substituted cycloalkyl) group;

halogen refers to fluoro, chloro, bromo and iodo;

heteroaryl refers to an aromatic group of from 1 to 10 carbon atoms and 1 to 4 heteroatoms selected from the group consisting of oxygen, nitrogen and sulfur within a single ring or multiple condensed rings;

substituted heteroaryl refers to a heteroaryl group substituted with from 1 to 3 substituents selected the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl or heterocyclic refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more of the rings can be cycloalkyl, aryl or heteroaryl provided that the point of attachment is through the heterocyclyl ring;

substituted heterocyclyl or heterocyclic refers to a heterocycle group substituted with from 1 to 3 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl;

substituted heterocyclyloxy refers to —O-(substituted heterocyclyl);

phosphate refers to a moiety selected from the group consisting of —OP(O)(OH)$_2$ (monophosphate), —OP(O)(OH)OP(O)(OH)$_2$ (diphosphate) and —OP(O)(OH)OP(O)(OH)OP(O)(OH)$_2$ (triphosphate) or salts thereof including partial salts thereof;

phosphonate refers to a moiety selected from the group consisting of —OP(O)(R)(OH), —OP(O)(OR), and salts thereof including partial salts thereof, wherein each R is independently selected from hydrogen, alkyl, substituted alkyl, carboxylic acid, and carboxyl ester;

sulfonate ester refers to —SO$_2$OR where R is selected from the group consisting of alkyl, substituted alkyl, alkenyl, substituted alkenyl, aryl, substituted aryl, heteroaryl, substituted heteroaryl, heterocyclyl and substituted heterocyclyl;

thiol refers to —SH;

thioalkyl or alkylthioether refers to —S-alkyl;

substituted thioalkyl refers to —S-(substituted alkyl);

thiocycloalkyl refers to —S—cycloalkyl;

substituted thiocycloalkyl refers to —S—(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclyl refers to —S-heterocyclyl; and substituted thioheterocyclyl refers to —S-(substituted heterocyclyl).

7. The compound according to claim 6, wherein at least one of R and R$^1$ is other than hydrogen.

8. A compound selected from the group consisting of:
   1-(2'-C-methyl-β-D-ribofuranosyl)-4-methoxylamino-pyrazolo[3,4-d]pyrimidine;
   1-(2'-C-methyl-β-D-ribofuranosyl)-4-hydroxylamino-pyrazolo[3,4-d]pyrimidine;
   1-(2'-C-methyl-β-D-ribofuranosyl)-3-bromo-4-hydroxylamino-pyrazolo[3,4-d]pyrimidine;
   1-(2'-C-methyl-β-D-ribofuranosyl)-3-methyl-4-hydroxylamino-pyrazolo[3,4-d]pyrimidine;
   1-(2'-C-methyl-β-D-ribofuranosyl)-3-cyano-4-hydroxylamino-pyrazolo[3,4-d]pyrimidine;
   1-(2'-C-methyl-β-D-ribofuranosyl)-4-methoxylamino-pyrazolo[3,4-d]pyrimidine-3-carboxamide;
   1-(2'-C-methyl-β-D-ribofuranosyl)-3-bromo-4-methoxylamino-pyrazolo[3,4-d]pyrimidine;
   1-(2'-C-methyl-β-D-ribofuranosyl)-3-methyl-4-methoxylamino-pyrazolo[3,4-d]pyrimidine;
   1-(2'-C-methyl-β-D-ribofuranosyl)-3-cyano-4-methoxylamino-pyrazolo[3,4-d]pyrimidine; and
   1-(2'-C-methyl-β-D-ribofuranosyl)-4-methoxylamino-pyrazolo[3,4-d]pyrimidine-3-carboxamide.

9. The compound according to any of claims 1, 5, and 6, wherein R$^{14}$ is hydrogen and R$^{13}$ is selected from the group consisting of alkyl and hydrogen.

10. The compound according to claim 9, wherein R$^{14}$ is hydrogen and R$^{13}$ is selected from the group consisting of hydrogen, methyl, ethyl, and n-propyl.

11. The compound according to any of claims 1, 5, and 6, wherein R is hydrogen and R$^1$ is selected from the group consisting of methyl, vinyl, allyl, acetylenyl, propargyl, and trifluoromethyl.

12. The compound according to any of claims 1, 5, and 6, wherein W is selected from the group consisting of hydrogen, acyl or triphosphate.

13. The compound according to any of claims 1 and 6, wherein W$^2$ and W$^3$ are hydrogen or acyl.

14. The compound according to claim 13, wherein W$^2$ is hydrogen or acyl and W$^3$ is hydrogen.

15. The compound according to claim 14, wherein W$^2$ is acyl.

16. The compound according to claim 15, wherein said acyl group is selected from the group consisting of acyl groups derived from amino acids, trimethylacetyl, and acetyl.

17. A pharmaceutical composition comprising a pharmaceutically acceptable diluent and a therapeutically effective amount of a compound or mixture of compounds according to any of claims 1, 3, 6, and 8.

18. A method for treating HCV in a mammal in need there of which method comprises administering to said mammal diagnosed with HCV a therapeutically effective amount of a pharmaceutical composition according to claim 17.

19. A method for treating HCV in a mammal in need thereof which method comprises administering to said mammal diagnosed with HCV a therapeutically effective amount of a compound or mixtures of one or more compounds according to any of claims 1, 5, 6 and 8.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aggacatgga tccgcggggt cgggcacgag acag                              34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
aaggctggca tgcactcaat gtcctacaca tggac                             35